(12) United States Patent
Tung

(10) Patent No.: US 10,792,249 B2
(45) Date of Patent: Oct. 6, 2020

(54) HIGH DRUG LOADING PHARMACEUTICAL COMPOSITIONS

(71) Applicant: Hsien-Hsin Tung, Scotch Plains, NJ (US)

(72) Inventor: Hsien-Hsin Tung, Scotch Plains, NJ (US)

(73) Assignee: AcrysPharm LLC, Scotch Plains, NJ (US)

( * ) Notice: Subject to any disclaimer, the term of this patent is extended or adjusted under 35 U.S.C. 154(b) by 23 days.

(21) Appl. No.: 15/803,372

(22) Filed: Nov. 3, 2017

(65) Prior Publication Data

US 2019/0021997 A1 Jan. 24, 2019

Related U.S. Application Data

(60) Provisional application No. 62/536,430, filed on Jul. 24, 2017.

(51) Int. Cl.
*A61K 9/10* (2006.01)
*A61K 9/14* (2006.01)
(Continued)

(52) U.S. Cl.
CPC ............... *A61K 9/10* (2013.01); *A61K 9/146* (2013.01); *A61K 31/192* (2013.01); *G01N 25/4866* (2013.01)

(58) Field of Classification Search
CPC .... G01N 25/12; G01N 25/14; G01N 25/4866; A61K 9/10; A61K 9/141; A61K 9/146
See application file for complete search history.

(56) References Cited

U.S. PATENT DOCUMENTS 6,787,157 B1 9/2004 Rosenberg et al.
8,258,132 B2 9/2012 Bosch et al.
(Continued)

FOREIGN PATENT DOCUMENTS

WO 1993020138 A2 10/1993

OTHER PUBLICATIONS

Dabbagh et al. Investigation of Solid Dispersion Technique in Improvement of Physicochemical Characteristics of Ibuprofen Powder. Iranian Journal of Pharamceutical Sciences, 2007:3(2):69-76. (Year: 2007).*

(Continued)

*Primary Examiner* — Lakshmi S Channavajjala
(74) *Attorney, Agent, or Firm* — Sarika Singh; McNeely, Hare & War LLP

(57) ABSTRACT

A pharmaceutical composition of high drug loading comprising an active pharmaceutical ingredient (API) and pharmaceutical acceptable additives, which include glass-solution forming additive and/or eutectic-mixture forming additive, is provided. The composition is dispersed uniformly to form a hybrid solid dispersion consisting of crystalline-suspension, glass-solution and/or eutectic-mixture, where the crystalline API is uniformly distributed in the hybrid solid dispersion and exists in nano/micro particle size range. The amorphous API, when present, is uniformly distributed in the hybrid solid dispersion. The API may exist in different chemical and/or physical forms. The API is present in an amount of from more than about 50% wt/wt to about 90% wt/wt with respect to the total amount of the active pharmaceutical ingredient and the pharmaceutically acceptable glass-solution forming and/or eutectic-mixture forming additives. At least about 50% wt/wt of the API is dispersed in the crystalline-suspension and at least about 5% wt/wt of the API is dispersed in the glass-solution and/or eutectic-mixture. The pharmaceutical composition offers excellent dissolution rate, superior chemical and physical stability, and minimum drug-drug/drug-excipient incompatibility. The composition is beneficial for reducing the overall tablet/capsule size for low water-soluble drugs requiring high drug loading or dosage, including combination drugs.

19 Claims, 9 Drawing Sheets

(51) Int. Cl.
*A61K 31/192* (2006.01)
*G01N 25/48* (2006.01)

(56) References Cited

U.S. PATENT DOCUMENTS

| | | | |
|---|---|---|---|
| 9,254,268 B2 | 2/2016 | Krayz et al. | |
| 2004/0185110 A1* | 9/2004 | Harland | A61K 9/146 424/489 |
| 2005/0019399 A1 | 1/2005 | Fischer et al. | |
| 2009/0012184 A1 | 1/2009 | Rosenberg et al. | |
| 2010/0222311 A1 | 9/2010 | Thommes et al. | |
| 2012/0213827 A1 | 8/2012 | Chatterji et al. | |
| 2015/0132385 A1 | 5/2015 | Bansal et al. | |
| 2015/0182457 A1* | 7/2015 | Huang | A61K 9/145 424/487 |
| 2016/0158245 A1 | 6/2016 | Dombret | |

OTHER PUBLICATIONS

M. Newa et al., 'Preparation, Characterization and In Vivo Evaluation of Ibuprofen Binary Solid Dispersions and Poloxamer 188', Int. J. Pharm, vol. 343, p. 228 (2007).
M. Newa et al.,'Enhanced Dissolution of Ibuprofen Using Solid Dispersion with Poloxamer 407', Arch. Pharm. Res., vol. 31, p. 1491 (2008).
M. Newa et al.,'Enhanced of Solubility, Dissolution and Bioavailability of Ibuprofen in Solid Dispersion Systems', Chem. Pharm. Bull., vol. 56, p. 569 (2008).
M. Newa et al.,'Enhanced Dissolution of Ibuprofen Using Solid Dispersion with Polyethylene Glycol 20000', Drug Development and Industrial Pharmacy, vol. 34, p. 1031 (2008).
S. Janssens et al., 'Characterization of Ternary Solid Dispersions of Itraconazole, PEG 6000, and HPMC 2910 E5', Journal of Pharmaceutical Sciences, vol. 97, p. 2110 (2008).
S. Janssens et al., 'Characterization of ternary solid dispersions of Itraconazole in polyethylene glycol 6000 / polyvidone-vinyl acetate blends', Eur. J. Pharm. Biopharm., vol. 69, p. 1114 (2008).
G.M.E. Maghraby et al., 'Synergistic Enhancement of Itraconazole Dissolution by Ternary System Formation with Pluronic F68 and Hydroxypropylmethylcellulose', Sci. Pharm. vol. 77, p. 401 (2009).
Y.J. Park et al., 'Development of Novel Ibuprofen-loaded Solid Dispersion with Improved Bioavailabilty using Aqueous Solution', Arch Pharm. Res., vol. 32, p. 767 (2009).
Y.J. Park et al., 'Development of Novel Itraconazole-loaded Solid Dispersion without Crystalline Change with Improved Bioavailability', Arch. Pharm. Res., vol. 33, p. 1217 (2010).
International Search Report and Written Opinion of the International Search Authority for PCT/US2017/060047 which shares the same priority as the present application.
Informal Comments of the Applicant in Response to the Written Opinion of the ISA for PCT/US2017/060047.

* cited by examiner

```
┌─────────────────────────────────────┐
│ Active Pharmaceutical Ingredients,  │
│ Glass-solution forming additive and/or │
│ Eutectic-mixture forming additive, and │
│ Solvent / solvents                  │
└─────────────────────────────────────┘
              ⇩ Crystallization or
                slurry approaches
┌─────────────────────────────────────┐
│ Uniform mixture of APIs,            │
│ additives & solvents                │
└─────────────────────────────────────┘
              ⇩ Solvents evaporation;
                batch or continuous
                approaches
┌─────────────────────────────────────┐
│ Hybrid solid dispersion —           │
│ Crystalline-suspension,             │
│ Glass-solution and/or               │
│ Eutectic-mixture                    │
└─────────────────────────────────────┘
```

Figure 1

HIGH DRUG LOADING PHARMACEUTICAL COMPOSITIONS

TECHNICAL FIELD

The present invention relates to high drug loading pharmaceutical compositions and methods of making the same. The compositions comprise active pharmaceutical ingredients in the form of hybrid solid dispersion.

BACKGROUND

Higher bioavailability of drugs may be obtained by achieving high drug loading, enhanced dissolution rate, maximum chemical and physical stability, and minimum drug-drug or drug-excipient incompatibility while preparing pharmaceutical compositions.

The amount of API or drug that can be included in a pharmaceutical composition is generally termed as drug loading. Drug loading may be expressed as % w/w with reference to the total weight of the pharmaceutical composition.

Different approaches have been reported across the pharmaceutical industry to improve the bioavailability of drugs or active pharmaceutical ingredients (APIs), especially for sparingly soluble drugs. One such approach involves solid dispersions in which drugs are dispersed with pharmaceutical acceptable additives.

Solid dispersion is a dispersion of drugs in a matrix in solid state, prepared by melting (fusion), solvent, or melting-solvent methods, as well as other non-traditional technique, such as co-grinding (Chiou et al., J. Pharm. Sci., 60(9), p 1281 (1971); Kaneniwa et al., (Chem. Pharm. Bull., 23, p 2973 (1975)). Dispersion of a drug or drugs in a solid diluent or diluents by traditional mechanical mixing is not considered a solid dispersion.

Solid dispersions can be generally grouped into the following categories—eutectic-mixtures, solid-solutions, crystalline-suspensions, glass-solutions, and glass-suspensions. For the eutectic-mixture, solid-solution and crystalline-suspension, APIs exist in crystalline solid state. The eutectic-mixtures, solid-solutions and crystalline-suspensions are therefore considered crystalline-based solid dispersions. For glass-solution and glass-suspension, APIs exist in an amorphous solid state. Glass-solutions and glass-suspensions are therefore considered amorphous-based solid dispersions (Leuner et al., Eur. J. Pharm. BioPharm, 50, p 47 (2000); Craig et al., Int. J. Pharm., 231, p 131 (2002); Singh et al., Int. J. Pharm. Life Sci., 2(9), p 1078 (2011)). Among these solid dispersions, crystalline-based solid dispersions possess better stability but inferior dissolution performance compared to amorphous-based solid dispersions (Brough et al., Int. J. Pharm., 453, p 157 (2013)).

For eutectic-mixtures, the drug loading is typically no more than 50% w/w without specific control of API particle size (Law et al., J. Pharm. Sci., 92, p 505 (2003); Cherukuvada et al., Chem. Comm. 50, p 906 (2014)). If the drug loading is above the eutectic composition, formation of solid dispersion can lead to non-uniformly distributed crystalline API and additives. This distribution is heavily affected by the crystallization kinetics and mixing during the crystallization.

For crystalline-suspensions, drug or API loading in a pharmaceutical composition can be greater than 50% w/w. However, achieving such high drug loading requires that API particles be within nano/micro particle size range in the crystalline-suspension (Kawabata et al., Int. J. Pharm., 420, p 1 (2011)). Also, crystalline API may be present in different chemical and physical forms, for example polymorphs, salts, cocrystals, solvate/non-solvate, hydrate/anhydrate, which may have varying degree of chemical/physical properties, such as solubility, hygroscopicity, stability and drug-excipient interaction. It can be challenging to control the crystallization of API with the desired chemical and physical forms, residual amorphous API supersaturation, distribution of API particles and particle size within the crystalline suspension.

Amorphous-based solid dispersions generally possess better dissolution performance due to the amorphous nature of the API. However, due to the amorphous nature of the API, amorphous-based solid dispersions have a higher degree of instability. If drug loading is higher than API's solubility in the glass-solution forming additive, it maybe kinetically stable over a certain period, but is thermodynamically unstable. This may require special manufacturing precautions, for example moisture control. Higher moisture levels can negatively reduce API solubility and glass transition temperature of the glass-solution, and trigger uncontrolled API crystallization in the glass-solution. Consequently, drug loading of such dispersions is generally no more than 50% w/w in order to reduce the risk of instability (Shah et al., 'Amorphous Solid Dispersions, Theory and Practice', Springer (2014); A. Newman editor, 'Pharmaceutical Amorphous Solid Dispersions,' Wiley (2015)).

Both crystalline-based and amorphous-based solid dispersions possess better drug-drug and drug-excipient compatibility than the conventional dry-blended drugs (Nie et al., Int. J. Pharm., 517, p 203 (2017)).

High drug loading, enhanced dissolution rate, maximum chemical and physical stability, and minimum drug-drug or drug-excipient incompatibility may be achieved through a combination of crystalline-based and optionally amorphous-based solid dispersions. However, proper design and control of the process of combining crystalline APIs and amorphous APIs with opposite physicochemical characteristics remains challenging.

SUMMARY

The present invention provides pharmaceutical compositions of high drug loading comprising active pharmaceutical ingredients, and pharmaceutical acceptable glass-solution forming and/or eutectic-mixture forming additives. The invention synergistically integrates a crystalline-suspension, a glass-solution and/or a eutectic-mixture, including a solid-solution, into one hybrid solid dispersion.

In particular, the pharmaceutical composition of the invention comprises:
 an active pharmaceutical ingredient; and
 pharmaceutically acceptable glass-solution forming additives, and/or
 pharmaceutically acceptable eutectic-mixture forming additives,
wherein the active pharmaceutical ingredient and the pharmaceutical acceptable additives are present in the form of a hybrid solid dispersion consisting of a uniformly distributed solid dispersion of:
 a crystalline-suspension; and
 a glass-solution and/or a eutectic-mixture,
wherein the active pharmaceutical ingredient is present in an amount of from more than about 50% w/w to about 90% w/w with respect to the total amount of the active pharmaceutical ingredient and the pharmaceutically acceptable glass-solution forming and/or eutectic-mixture forming additives in the pharmaceutical composition, wherein about 50% w/w to about 95% w/w of the active pharmaceutical ingredient is dispersed in the crystalline-suspension and the remaining active pharmaceutical ingredient is dispersed in the glass-solution and/or the eutectic-mixture, wherein crystalline active pharmaceutical ingredient exists in a nano/micro particle size range and is uniformly distributed in the hybrid solid dispersion, and wherein amorphous active pharmaceutical ingredient, when present, is uniformly distributed in the hybrid solid dispersion.

The method for making the pharmaceutical composition comprises:

generating a uniform suspension of nano/micro size particles of the API crystals in one or more solvents containing partially dissolved API and fully dissolved pharmaceutical acceptable glass-solution forming and/ or eutectic-mixture forming additives; and evaporating the solvents from the suspension to obtain dry solid particles.

The suspension can be generated by crystallization of the API from a solution, or slurrying the API crystals in one or more solvents, or a combination of both.

Dispersion of a drug or drugs in a solid diluent or diluents by traditional mechanical mixing does not produce a solid dispersion and is termed herein as a "physical mixture."

The distribution of the API in the hybrid solid dispersion is controlled by the level of the glass-solution forming and/or eutectic-mixture forming additives in the composition, ratio of dissolved and undissolved API in the solvent mixture, and the process of making the hybrid solid dispersion. The API dispersed in the glass-solution and/or eutectic-mixture is believed to be primarily from the dissolved API. A portion of undissolved API may or may not be incorporated into the eutectic-mixture. The API dispersed in the crystalline-suspension is believed to be primarily from the remaining undissolved API.

The API dispersed in the hybrid solid dispersion can exist in different chemical and physical forms. The API in the crystalline-suspension may exist as a salt, co-crystal, solvate, or hydrate, and different crystalline forms of the above. The API in the glass-solution and/or eutectic-mixture may exist as non-ionized, non-polarized, non-solvated, or non-hydrated free molecule, and the like.

The pharmaceutical composition of the invention realizes key benefits of solid dispersion, i.e. superior dissolution rate of glass-solution and/or eutectic-mixture, excellent stability of a crystalline-based solid dispersion, and reduced drug-drug or drug-excipient interaction characteristic of a solid dispersion in general, especially in case of high drug loading.

Furthermore, the pharmaceutical composition of the invention facilitates development of combination drugs. High drug loading of an API as a hybrid solid dispersion can be blended with other APIs, whether or not in a hybrid solid dispersion form, into a single dosage form, for example direct filled capsule without additional non-functional excipients or direct compression tablet with minimum film coating, etc. The single dosage will have minimum drug-drug incompatibility and excellent dissolution & bioavailability. It also reduces overall capsule/tablet number and size beyond the tedious and expensive multiple tablet/capsule approaches. Therefore, it offers a convenient and effective alternative to treat diseases, for example pain, cancer and others, which require treatment of multiple drugs and/or high drug dosage over time.

BRIEF DESCRIPTION OF THE DRAWINGS

FIG. 1 provides a flowchart depicting a summary of the overall process design for preparing an embodiment of the hybrid solid dispersion of the invention.

DETAILED DESCRIPTION

Starting Materials

Figure 2:
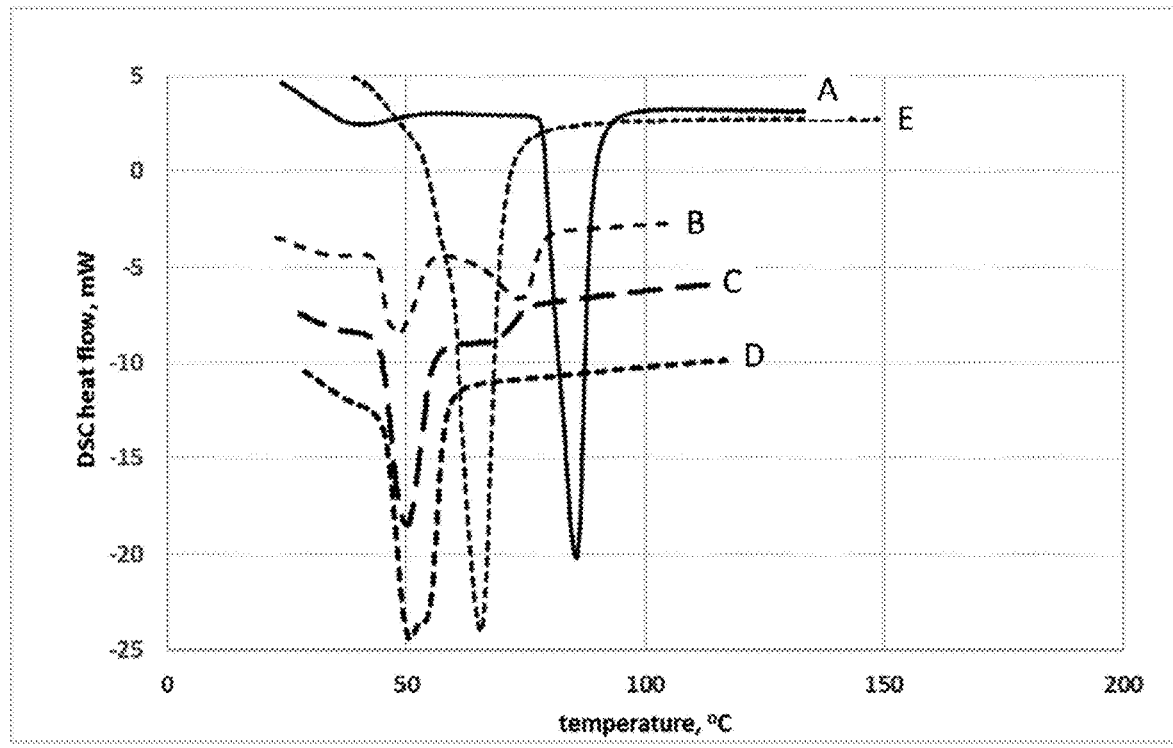
FIG. 2 shows DSC profile of pure ibuprofen (curve A), pure poloxamer 188 (curve E) and physical mixtures of ibuprofen/poloxamer having w/w ratios of 4/1 (curve B), 1/1 (curve C), and 1/4 (curve D).

The pharmaceutical composition of the invention comprises an active pharmaceutical ingredient (API), pharmaceutical acceptable glass-solution forming additives and/or eutectic-mixture forming additives.

The active pharmaceutical ingredient of the invention can be any API which can exist as a crystalline solid at room temperature. The invention is particularly useful for APIs that have low water solubility and/or those which are chemically or physically unstable. Examples of some APIs include aceclofenac, amlodipine, amiodarone, albendazole, atovaquone, cefixime, danazol, felodipine, fenofibrate, griseofulvin, ibrutinib, ibuprofen, itraconazole, ketoprofen, ketoconazole, loratadine, nevirapine, nimesulide, probucol, sorafenib, troglitazone, ubiquinone, and valsartan.

The amount of API in the composition is greater than about 50% w/w but no more than about 90% w/w with respect to the total amount of the active pharmaceutical ingredient and the pharmaceutically acceptable glass-solution forming and/or eutectic-mixture forming additives.

The glass-solution forming additives are well known in the art, such as those disclosed in Shah et al., '*Amorphous Solid Dispersions, Theory and Practice*', Springer (2014) and A. Newman editor, '*Pharmaceutical Amorphous Solid Dispersions*,' Wiley (2015), and can be any pharmaceutical acceptable additive which can solubilize the API to some extent. The range of API solubility in these additives may be determined by routine experimentation in order to select the proper additive candidate.

Commonly used glass solution additives include polymers, such as PVP, PVP-VA, MAA-MMA (poly(methacrylic acid-co-methyl methacrylate)), HPMC, and HPMCAS, as well as surfactants comprising anionic sulfate/sulfonate/carboxylate, cationic ammonium, nonionic glycerol ester/ether/block copolymer (poloxamer). Commercial available glass-solution pharmaceutical products include NuvaRing® comprising etonogestrel and ethyl estradiol (APIs) and ethyl vinyl acetate (additive), Kaletra® comprising lopinavir and ritonavir (APIs) and polyvinylpyrrolidone/vinyl acetate (PVP-VA, additive), Incivek® comprising telaprevir (API) and hypromellose acetate succinate (HPMCAS, additive).

The eutectic-mixture forming additives are well known in the art and can be any pharmaceutical acceptable additives which form a eutectic-mixture with the desired API. For example, see Gala et al., *J. Develop Drugs*, 2, p 130 (2013). The feasibility of an additive to form the eutectic-mixture with API can be determined by routine experimentation using differential scanning calorimetry. Many eutectic-mixture forming additives can also form a solid-solution with the API when the content of the mixture approaches pure API or pure additive. Such solid-solution forming property of the additive does not exclude it from qualifying as a eutectic-mixture forming additive of the invention.

For example, polyethylene glycol (PEG) polymers can form eutectic-mixture with various APIs including ibuprofen, naproxen, fenofibrate, and indomethacin (Law et al., *Pharm. Res.* 19 (3), p 315 (2002)). Examples of some eutectic-mixtures include thymol/ibuprofen (3/2, additive/API ratio); PEG/genistein 24/1; and menthol/borneol 3/1; pyrazinamide/isoniazid (1/1); and succinic acid/pyrazinamide/isoniazid (1/1/1).

Eutectic-mixture forming additives do not exclude other APIs or co-crystals. Fundamentally, for any crystalline API which consists of least one chiral center in its molecular structure, the two enantiomeric isomers of the API could form a eutectic-mixture with each other as conglomerate, and so can the corresponding salts of the API with achiral or chiral counter-ions. Also, cocrystal forming additive may also form eutectic-mixtures with the API. For example, Nicotinamide forms a co-crystal, as well as eutectic-mixtures with both flurbiprofen and ibuprofen (Chow et al., *Pharm. Res.*, 29, p 1853 (2012)).

The eutectic-mixture forming additive and glass-solution forming additive can be partially miscible. The API solubility in the glass-solution forming additive may or may not be affected in the presence of eutectic-mixture forming additive, and the eutectic composition of API with the eutectic-mixture forming additive may or may not be affected in the presence of glass-solution forming additive. The ternary phase map can be determined experimentally via conventional tools such as DSC, PXRD and/or polarized light microscopy (Gumaste, et al., The AAPS Journal, 18 (5), p 1131 (2016)).

The glass-solution forming additives and/or eutectic-mixture forming additives in the composition may be greater than about 10% w/w but less than about 50% w/w with respect to the total amount of the active pharmaceutical ingredient and the pharmaceutically acceptable glass-solution forming additives and/or eutectic-mixture forming additives.

The solvents used in the preparation process can be water and/or any organic solvent listed in The International Conference on Harmonisation of Technical Requirements for Registration of Pharmaceuticals for Human Use (ICH) class 2 or 3, or mixtures of them. ICH class 3 solvents are preferred over class 2 solvents due to less toxicity. Class I solvents are excluded from this invention.

Suitable APIs have partial solubility in the selected solvent or solvent mixture at the operating temperature. Glass-solution forming additives and eutectic-mixture forming additives are completely soluble/miscible in the selected solvent or solvent mixture at the operating temperature.

Process

Making the desired hybrid solid dispersion comprises two key steps as described below.

1. Generating a uniform mixture of API, additive(s) and solvent(s) through proper procedures. The mixture comprises undissolved crystalline API, fully dissolved additive(s) in the solvent(s) and dissolved API in the solvent(s). No less than about 50% w/w of the total API is in undissolved crystalline form and no less than about 5% of the total API may be in dissolved form.
2. Evaporating solvent(s) off from the mixture in step 1 above to form solid particles of a hybrid solid dispersion, and optionally delumping the solid particles obtained after drying.

In the first step the mixture can be prepared by using a crystallization method. The API is dissolved in the selected solvent or solvents and then crystallized out from the solution. Through this step, API crystals of desired crystal form, particle size distribution, and morphology may be generated. It is fully expected that variables such as seeding, generation of supersaturation, and control of mixing can have profound impact on the resulting API crystals. Therefore, it is critical to control these variables to generate crystalline API with desired attributes. For example, if it is desirable to have fine particles in the sub-micron or less than 20-30 micron range, high supersaturation to promote nucleation with intensive mixing may be required during the crystallization of some APIs. Impinging jet crystallization may be employed for such results. However, for some other APIs, identical level of supersaturation could lead to formation of amorphous API, oily/liquid droplets with high API concentration, or API crystals with metastable form. Therefore, the range of supersaturation for specific APIs is suitably adjusted to avoid these complications.

Inadequate mixing can lead to non-uniform distribution of supersaturation in the solution and consequently lead to undesirable forms in the mixture such as non-uniform amorphous solids, oils, metastable forms, nucleation, particle agglomeration, etc. To overcome these complications, intensive mixing, such as impinging jet, high shear/speed mixer, sonicator, and the like may be used.

In the first step, the mixture can also be prepared by a slurry method. API crystals are mixed with the selected solvents to form a slurry. Since the starting crystalline API may not meet the desired crystal form, particle size distribution, or morphology requirements, additional considerations may be required. For example, if the existing API has an undesired crystal form, it is necessary to select a proper solvent system in which the undesired crystal form is metastable and can convert to the desired stable crystal form. If the starting API crystal particle size is too big, then a bead mill, high shear/speed mixer, or sonicator etc. can be used to grind the particles. If the starting API crystals have long needle morphology with a high aspect ratio, then a high shear/speed mixer or sonicator etc. with multiple cycles of heating and cooling of the entire batch can be utilized to reduce the particle size and improve the aspect ratio.

In the first step, a combination of crystallization and slurry approaches can also be implemented. For example, after completing crystallization in a solvent(s), the slurry is filtered. The resulting wet cake is then washed and re-suspended in a different solvent(s).

A portion of API needs to remain dissolved in the solvents in step 1. The type and composition of the solvents, the amount of solvents or batch temperature can be adjusted to increase or decrease the amount of dissolved API in the solvents. For example, if too little API is dissolved in the solvents, a small amount of solvent with high API solubility can be added to the mixture after the crystallization process to dissolve more API. Alternatively, the temperature of mixture can be increased after the crystallization to increase the API solubility in the solvents.

The dissolved API can be in a different chemical and physical form from the undissolved API. For example, if the API contains an acidic group in its chemical structure, the free acid may be soluble in non-polar solvents and its sodium salt may be insoluble in non-polar solvents. Accordingly, if non-polar solvents are used, the dissolved API may be in the free acid form and undissolved API crystals may be present as the sodium salt. Furthermore, the undissolved sodium salt can be unsolvated, or in the form of a solvate, or in different polymorphic forms thereof. Similarly, sodium salt or a cocrystal may have high solubility in aqueous solution, and the free acid may be practically insoluble in an aqueous solution. In such a case, if an aqueous solution is used, the dissolved API may be a sodium salt or a cocrystal and the undissolved API crystals may be in the free acid. Additionally, the undissolved free acid can be a hydrate, anhydrate, or different polymorphs thereof.

In the second step, solvent or solvents from the mixture of the first step are removed by evaporation, preferably under vacuum in the presence of an inert gas. At this stage, the glass-solution forming additive can precipitate out with the dissolved API to form an amorphous glass-solution and/or the eutectic-mixture forming additive can co-crystallize out with dissolved API to form a eutectic-mixture. Upon forming, the eutectic-mixture may or may not incorporate a portion of the undissolved API as well. The remaining undissolved crystalline API is uniformly dispersed in the glass-solution and/or the eutectic-mixture to form a crystalline-suspension. These solid dispersions thus integrate to form a uniform hybrid solid dispersion.

The entire mixture from the first step can be dried in a vacuum dryer in a batch process approach. Agitation during the batch drying process is preferred to facilitate drying rate and ensure batch homogeneity. Alternatively, a stream of batch can be continuously fed into a dryer, where the solvent or solvents are evaporated and the dried solids particles are collected in a collection container. Continuous drying is the preferred approach because it provides more efficient drying rate and better control of the solid characteristics of the dry particles.

A combination of batch and continuous approach may also be employed. For example, after completing the continuous approach which removes the bulk of the solvents, the batch is then placed in a batch dryer to remove the final residual solvents from the solid particles.

In some embodiments,
i) the active pharmaceutical ingredient and the glass-solution and/or eutectic-mixture forming additive(s) are dissolved in one or more solvents and rapidly mixed with an anti-solvent using an impinging jet mixer;

ii) the slurry obtained in step a) is stirred below ambient temperature to at least partially crystallize the active pharmaceutical ingredient;

iii) the crystalline suspension obtained from step b) is optionally warmed to re-dissolve a portion of the crystallized active pharmaceutical ingredient; and iv) the crystalline suspension from step b) or c) is spray dried under vacuum at or above ambient temperature to obtain the hybrid solid dispersion.

In some specific embodiments, the API and the glass-solution and/or eutectic-mixture forming additive(s) are dissolved in a solvent(s) and rapidly mixed with an anti-solvent, such as water, using an impinging jet mixer; resulting slurry is stirred using a stirrer for several hours at a temperature of 0 to 5° C., optionally warmed to re-dissolve a portion of the crystallized API, and then spray dried under vacuum at a temperature of 35 to 40° C., to obtain the hybrid solid dispersion, which may then be stored in a desiccator.

Furthermore, an optional delumping step after drying may be added. For example, after drying, if the dried solid particles contain appreciable solid granules, these granules can be delumped via using a sieve, by co-milling, and the like to improve dry particles' solid flow properties and content uniformity.

Product

The dry solid particles of hybrid solid dispersion obtained after the two step process of the invention comprise a uniformly distributed crystalline-suspension, a glass-solution and/or a eutectic-mixture.

The API distribution in the hybrid solid dispersion is determined by the starting material composition and the process design. The API dispersed in the glass-solution and/or eutectic-mixture is believed to be primarily from the dissolved API in the first step of the process. Depending upon the starting pharmaceutical composition and process design, a portion of the undissolved API may or may not be incorporated into the eutectic-mixture. The API dispersed in the crystalline-suspension is believed to be primarily from the remaining undissolved API. About 50% w/w to about 95% w/w of the API is dispersed in the crystalline-suspension and the remaining active pharmaceutical ingredient is dispersed in the glass-solution and/or the eutectic-mixture.

In some embodiments, about 50% w/w to about 90% w/w of the active pharmaceutical ingredient is dispersed in the crystalline-suspension and the remaining active pharmaceutical ingredient is dispersed in the glass-solution and/or the eutectic-mixture.

In some embodiments, the active pharmaceutical ingredient is present in an amount of from more than about 50% w/w to about 85% w/w with respect to the total amount of the active pharmaceutical ingredient and the pharmaceutically acceptable glass-solution forming and/or eutectic-mixture forming additives in the pharmaceutical composition. In some other embodiments, the active pharmaceutical ingredient is present in an amount of from more than about 50% w/w to about 80% w/w with respect to the total amount of the active pharmaceutical ingredient and the pharmaceutically acceptable glass-solution forming and/or eutectic-mixture forming additives in the pharmaceutical composition. In yet other embodiments, the active pharmaceutical ingredient is present in an amount of from about 55% w/w to about 90% w/w, or about 60% w/w to about 90% w/w, or about 65% w/w to about 90% w/w, or about 65% w/w to about 85% w/w, or about 67% w/w to about 80% w/w, with respect to the total amount of the active pharmaceutical ingredient and the pharmaceutically acceptable glass-solution forming and/or eutectic-mixture forming additives in the pharmaceutical composition.

As controlled by the $1^{st}$ and $2^{nd}$ step of the process, the crystalline API exists in a nano/micro particle size range and is uniformly distributed in the hybrid solid dispersion, and the amorphous active pharmaceutical ingredient, when present, is also uniformly distributed in the hybrid solid dispersion.

Moisture has a profound impact on API solubility in the glass-solution forming additive and can lead to instability of a glass-solution. In such instances, the presence of a eutectic-forming additive, which is uniformly dispersed with glass-solution forming additive in the first step of the process, can effectively mitigate the risk of ill-controlled crystallization of amorphous API in the glass-solution and can convert it to crystalline API and form uniformly dispersed eutectic-mixture.

The integrated hybrid solid dispersion can contain the API in different chemical and physical forms. As described in the first process step above, the undissolved API can exist in one chemical and physical form and the dissolved API can exist in a different chemical and physical form.

The hybrid solid dispersion can be used as such to prepare a dosage form, such as a direct-filled capsule without adding additional excipients, or a direct-compaction tablet by adding a coating, if required.

In some embodiments, the pharmaceutical composition of the invention may comprise additional ingredients, such as binders, fillers, lubricants, disintegrants, controlled release agents, flavors, and film coating agents to form conventional dosage forms, such as tablets and capsules, using conventional techniques, such as granulation or direct compression.

In some embodiments, the pharmaceutical compositions of the invention may be blended with other APIs, whether or not in a hybrid solid dispersion form, into a single dosage form for fixed dose combination or combination drugs.

In certain embodiments, pharmaceutical compositions consist essentially of an active pharmaceutical ingredient; and pharmaceutical acceptable glass-solution forming additives, and/or pharmaceutical acceptable eutectic-mixture forming additives, and the number and amount of additional ingredients is minimized such that the essential characteristics and advantages of the hybrid solid dispersions of the invention are maximized.

EXAMPLES

Conventional analytical tools include the microscope, differential scanning calorimeter (DSC), powder X-ray diffractometer (PXRD), Raman spectrometer, particle size analyzer, Ultraviolet (UV)/Visible spectrometer, High Performance Liquid Chromatography (HPLC), in-vitro dissolution apparatus and testing protocols, etc. These tools may be used to characterize and analyze the performance of APIs, physical mixtures, conventional solid dispersions and hybrid solid dispersions of the invention.

For impinging jet crystallization process, the method of Tung et al. was followed ('Crystallization of Organic Compounds, An Industrial Perspective', Wiley (2009); Org. Process Res. Dev., 17, p 445 (2013)). Briefly described, a batch stream which contains dissolved API and solvent, and the anti-solvent stream which may contain dissolved additive and an anti-solvent (solvent in which the API is insoluble) are rapidly impinged against each other under high velocities at the selected temperature. The impingement enables rapid mixing of the two streams and generates a highly supersaturated solution in fractions of a second. This leads to the formation of desired nano/micro size API crystals with narrow particle size distribution.

Dissolutions were conducted as per the protocol described by Newa et al. (Int. J. Pharm., 343, p 228 (2007)). Newa et al. demonstrate that the in-vitro dissolution protocol correlates well with in-vivo bioavailability. Solid dispersion particles comprising 10 mg equivalent of ibuprofen is charged to a dissolution type II vessel at a paddle speed of 50±5 rpm, and temperature of 38±2° C., with 900 ml deionized (D.I.) water at pH of about 7.0 without pH buffer adjustment.

For examination of the dispersions under the microscope, procedure developed by Law et al. (J. Pharm. Sci., 92, p 505 (2003) was followed. A pinch of the solid dispersion was placed on the microscopic plate with a cover slide. One or two small drops of water, as the dispersing liquid, were carefully added to the edge of the cover slide via a pipette. The cover slide was gently tapped as needed to disperse the solid particles with water.

In the following examples, ibuprofen, which exists as a racemic compound and has low water solubility, is used as the representative API; poloxamer 188 and poloxamer 407 are used as representative eutectic-mixture forming additives; and hydroxypropyl methylcellulose (HPMC) and Eudragit® EPO are used as representative glass-solution forming additive. Racemic ibuprofen sodium dihydrate and ibuprofen sodium anhydrate, which exists as a racemic mixture or conglomerate of R-ibuprofen sodium and S-ibuprofen sodium, are used as the representative APIs having different chemical and physical forms in comparison to ibuprofen in its original form.

Example 1—Ibuprofen/Poloxamer 188 (API/Eutectic-Mixture Forming Additive) Solid Dispersions Poloxamer 188 can form a eutectic-mixture with ibuprofen with 30%-50% of ibuprofen and 50%-70% of poloxamer. At a weight ratio of 1/1 ibuprofen/poloxamer, the composition is sufficiently close to the eutectic composition. At weight ratios of 2/1 ibuprofen/poloxamer or higher, the drug loading exceeds the eutectic composition.

Conventional Eutectic-Mixture Solid Dispersion Preparation

Conventional solid dispersions listed in Table 1 were prepared as examples of solid dispersions known in the art by using melting method of Newa et al., *Int. J. Pharm.*, 343, p 228 (2007); *Arch. Pharm. Res.*, 31, p 1491 (2008); *Chem. Pharm. Bull.*, 56, p 569 (2008); *Drug. Dev. Ind. Pharm.*, 34, p 1031 (2008). Ibuprofen and poloxamer were carefully weighed and placed into the glass vial. The vial was then placed into a shaker heated at a temperature of 95° C. The solids were melted completely and rigorously mixed for 15 minutes at a rotation of 1200 rpm. The vial was removed from the shaker and cooled in a freezer at −20° C. After aging overnight, the vial was removed from the freezer and placed at ambient temperature. The solid mass in the vial was removed by spatula, ground with pestle mortar, and stored at ambient temperature in a desiccator.

TABLE 1

Ibuprofen/Poloxamer-Composition of Conventional Dispersions

| Ibuprofen/poloxamer 188 (w/w) | Ibuprofen (gram) | poloxamer 188 (gram) |
|---|---|---|
| 1/1 | 2 | 2 |
| 2/1 | 2 | 1 |

Preparation of Hybrid Solid Dispersion of the Invention

The solid dispersions listed in Table 2 were prepared by employing impinging jet crystallization. For the batch stream, ibuprofen was carefully weighed and dissolved in methanol at 0 to 5° C. For the anti-solvent stream, poloxamer was carefully weighed and dissolved in water at 0 to 5° C. The batch stream and anti-solvent stream were rapidly mixed via a "Y" shaped impinging jet mixer and the resulting mixed stream was collected in a glass vial at 0 to 5° C. with magnetic stirring. At this temperature, the supersaturation ratio (solution concentration/API solubility) would be about 50 which promoted rapid nucleation of ibuprofen. The resulting slurry was aged for a few hours to ensure complete release of supersaturation and crystallization of API. Then the slurry was warmed up to 35 to 40° C. to re-dissolve a portion of the ibuprofen crystals in the slurry. The slurry was then fed continuously through a custom spray nozzle into a glass collector under full vacuum at 35 to 40° C., where solvents were evaporated off from the atomized slurry droplets and the dry solid particles were collected. The dry solid particles of the obtained hybrid solid dispersion were removed from the collector and stored at ambient temperature in a desiccator.

TABLE 2

Ibuprofen/Poloxamer-Composition of Hybrid Dispersions

| Ibuprofen/poloxamer 188 (w/w) | Batch Stream | | Anti-solvent Stream | | |
|---|---|---|---|---|---|
| | Ibuprofen (gram) | MeOH (gram) | poloxamer (gram) | Water (gram) | Temperature (° C.) |
| 2/1 | 0.4 | 2 | 0.2 | 1 | 0-5 |
| 4/1 | 0.4 | 2 | 0.1 | 1 | 0-5 |

Characterization

Differential scanning calorimetric (DSC) profiles provide thermal behavior of components of a solid mixture. DSC profiles of ibuprofen, poloxamer 188, and physical mixtures of ibuprofen and poloxamer 188 at 4/1, 1/1 and 1/4 w/w ratios were recorded (FIG. 2) as reference standards. Physical mixtures of ibuprofen and poloxamer 188 at 4/1, 1/1 and 1/4 w/w ratios were prepared by blending ~200 mgs physical mixture each in 10 ml vial using a vortex mixer at 3000 rpm for a few minutes.

Pure ibuprofen and poloxamer show sharp large melting endotherms around 90° C. (curve A) and 65° C. (curve E), respectively. For all physical mixtures (curves B-D), a new melting endotherm around 45 to 50° C. appears. This corresponds to the melting of ibuprofen/poloxamer eutectic-mixture. For the physical mixture of ibuprofen/poloxamer (1/4), a second shoulder around 55° C. is observed (curve D). This is believed to be the melting of poloxamer 188, which decreases from 65° C. to 55° C. For the physical mixture of ibuprofen/poloxamer (4/1), the melting point of crystalline ibuprofen also decreases from 90° C. to 70-75° C. (curve B), associated with a significant reduction of melting endotherm. For the physical mixture of 1/1 ratio, which is close to the eutectic composition, a small endotherm around 70-75° C. of ibuprofen is still observed (curve C). This implies that a small fraction of ibuprofen remains and does not form the eutectic-mixture. Decrease of melting points of pure API and additive with reduced melting endotherms are typical thermal behavior of a eutectic-mixture.

Figure 3:
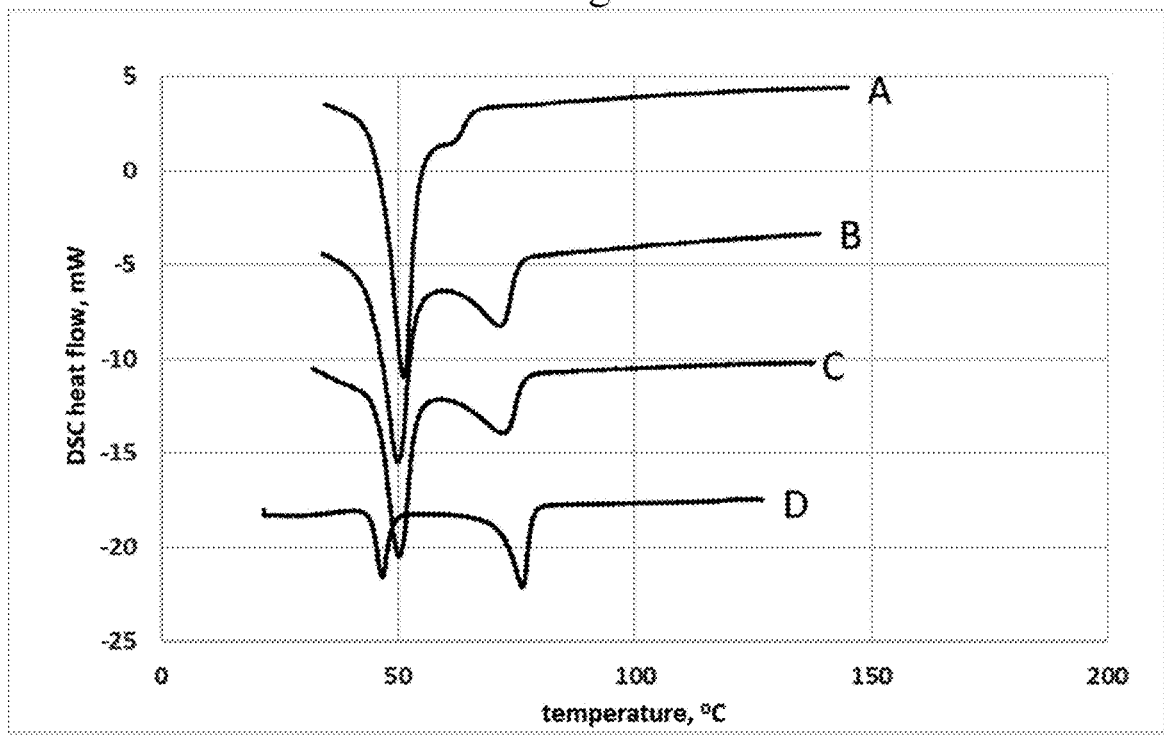
FIG. 3 shows DSC profile of ibuprofen and poloxamer 188 solid dispersions where curves A and B depict the DSC profiles of conventional solid dispersions having ibuprofen/poloxamer w/w ratios of 1/1 and 2/1, respectively, and curves C and D depict the DSC profiles of hybrid solid dispersions of the invention having ibuprofen/poloxamer w/w ratios of 2/1 and 4/1, respectively.

The DSC profiles of conventional solid dispersions of Table 1 and hybrid solid dispersions of the invention of Table 2 prepared above are shown in FIG. 3. The DSC profiles clearly show an endotherm around 45-50° C., corresponding to the melting of ibuprofen-poloxamer eutectic-mixture, and an endotherm around 70-75° C., corresponding to the melting of crystalline ibuprofen. Their individual endothermic values and the calculated levels of ibuprofen in crystalline-suspension and eutectic-mixture, based upon Janssens' procedure, (J Pharm Sci, 97, p 2110 (2008); Eur. J. Pharm. Biopharm., 69, p 1114 (2008)), are shown in Table 3.

TABLE 3

Ibuprofen/Poloxamer 188-Percentage of API in Crystalline-Suspension and Eutectic-Mixture

| Ibuprofen/poloxamer Ratio & Description | ΔH, Joules/gram around 45-50° C. | API in Eutectic-Mixture (%) | ΔH, Joules/gram around 70-75° C. | API in Crystalline-Suspension (%) |
|---|---|---|---|---|
| 1/1 conventional eutectic mixture dispersion, Curve A | ~80 | 95% or higher | <3 | <5% |
| 2/1 conventional eutectic mixture dispersion, Curve B | ~50 | ~50% | ~35 | ~50% |
| 2/1 hybrid dispersion of the invention, Curve C | ~50 | ~50% | ~35 | ~50% |
| 4/1 hybrid dispersion of the invention, Curve D | ~30 | ~25% | ~65 | ~75% |

As expected, at 1/1 ratio of ibuprofen/poloxamer, in a conventional dispersion, ibuprofen primarily forms the eutectic-mixture with a small fraction of ibuprofen forming a crystalline-suspension.

For both the conventional and hybrid dispersions at 2/1 ratio, the DSC profiles are nearly identical and the percentages of ibuprofen in crystalline-suspension and eutectic-mixture are very similar as well. The percentage of ibuprofen in crystalline-suspension is estimated to be about 50% and the percentage of ibuprofen in eutectic-mixture is estimated to be about 50%. For the hybrid dispersions of the invention at 4/1 ratio, the percentage of ibuprofen in crystalline-suspension is estimated to be about 75% and the percentage of ibuprofen in eutectic-mixture is about 25%. These dispersions do not contain glass-solution forming additive. The resulting DSC endotherm values and API material balance suggest the percentage of amorphous ibuprofen in both the conventional and hybrid dispersions is negligible.

These results demonstrate that the percentages of API in crystalline-suspension and eutectic-mixture can be varied by adjusting the ratio of API and eutectic forming additive in both conventional and hybrid dispersion approaches. However, as described below, there are vast differences between the properties of the dispersions formed by the two approaches in terms of dissolution, stability and distribution of API particles and particle size.

Dissolution Profile

Figure 4:
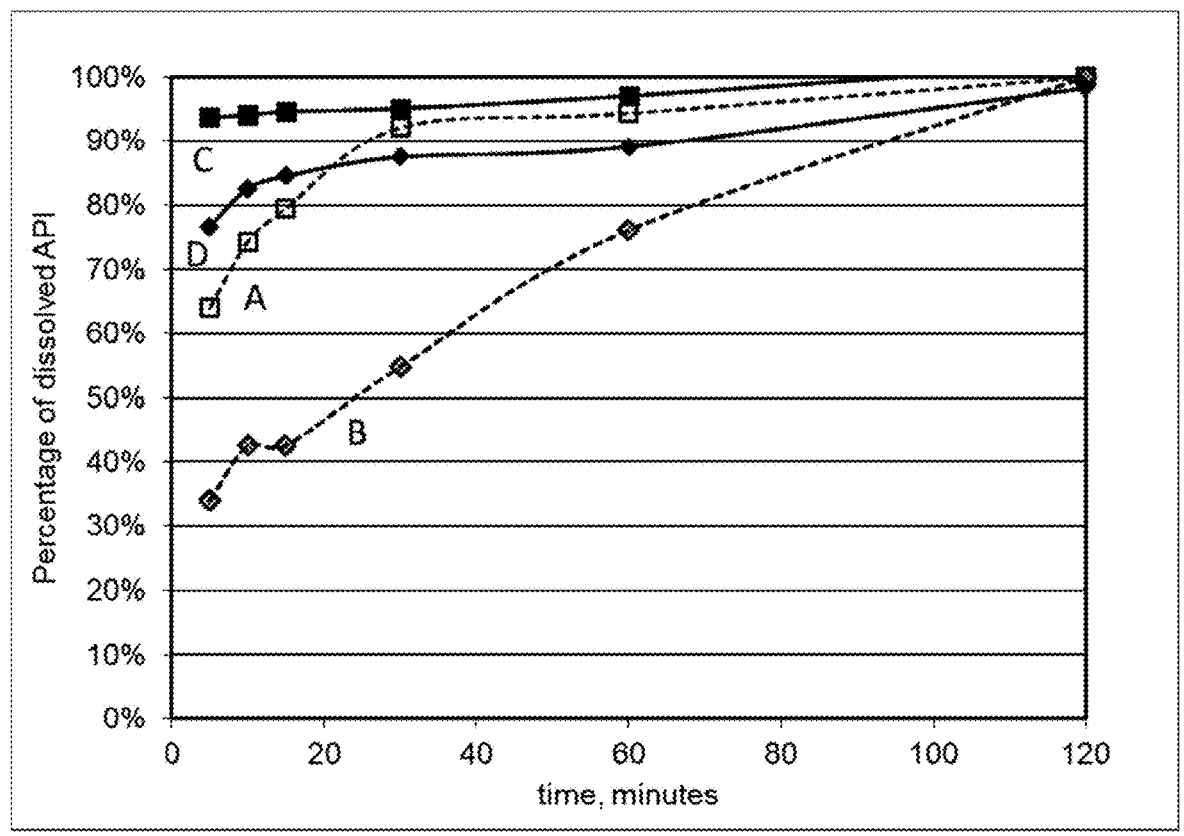
FIG. 4 shows dissolution profiles of ibuprofen and poloxamer 188 solid dispersions where dotted curves A and B show dissolution profiles of conventional solid dispersions having ibuprofen/poloxamer w/w ratios of 1/1 and 2/1, respectively, and curves C and D depict the dissolution profiles of hybrid solid dispersions of the invention having ibuprofen/poloxamer w/w ratios of 2/1 and 4/1, respectively.

As shown in FIG. 4, the dispersion of the invention at 2/1 ratio (ibuprofen/poloxamer) exhibits a more rapid dissolution profile (curve C) than those of the conventional dispersions at 1/1 and 2/1 ratios (curves A and B, respectively). The dispersion of the invention at 4/1 ratio exhibits a comparable dissolution profile (curve D) to that of the conventional dispersion at 1/1 ratio, and a more rapid dissolution profile than that of conventional dispersion at 2/1 ratio.

These dissolution results show that the dispersions of the invention achieve faster dissolution despite high drug loading of a low solubility API, thereby demonstrating the effectiveness of the hybrid solid dispersion of the invention in overcoming the limitation of eutectic compositions produced by traditional approaches.

Stability

Figure 5:
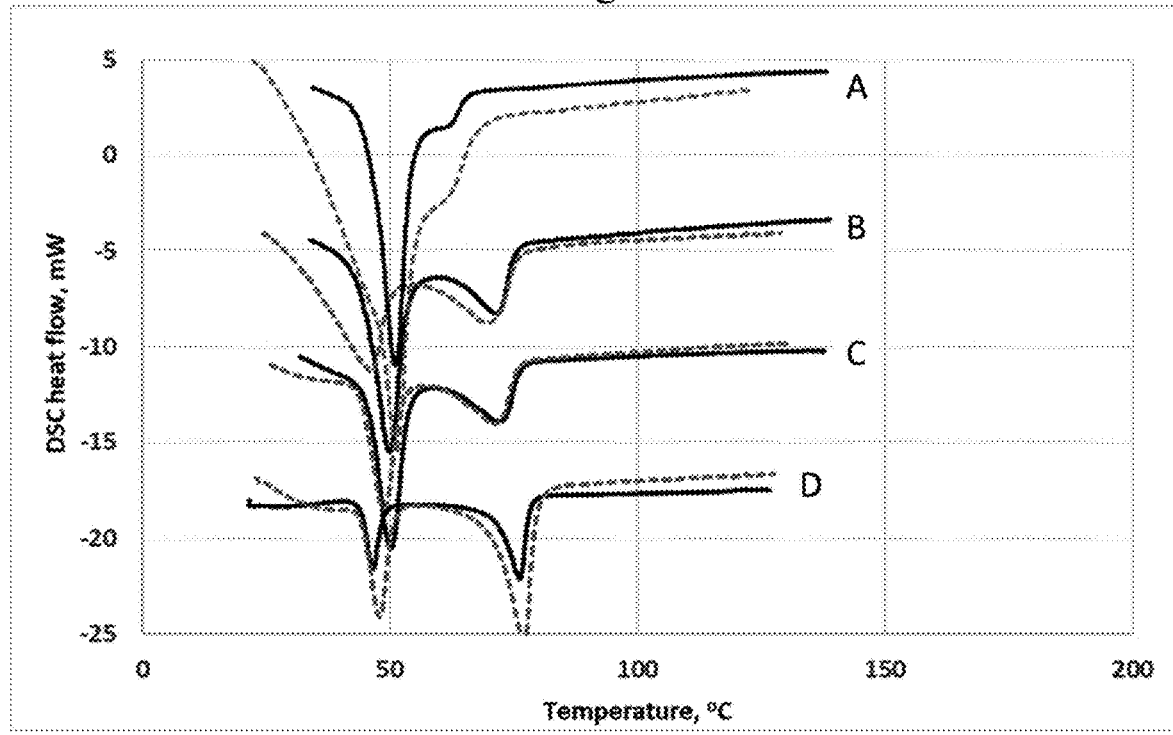
FIG. 5 shows the same DSC profiles as FIG. 3 except that conventional solid dispersions and the dispersions of the invention are stress tested at 40° C./75% RH and DSC profiles of the corresponding stress tested dispersions are recoded as dotted line curves, superimposed on the solid lines depicting the initial dispersions.

Samples of conventional dispersions and dispersions of the invention are stored in open vials at 40° C./75% RH chamber for one month to stress-test the samples' stability. FIG. 5 shows the same DSC profiles as FIG. 3 except that DSC profiles of the corresponding stress tested dispersions are recoded as dotted line curves, superimposed on the solid lines depicting the initial dispersions. As shown in FIG. 5, there are noticeable changes in DSC profiles of the conventional dispersions (curves A and B). The onset of $1^{st}$ endotherms is noticeably shifted toward a lower temperature at the beginning of the DSC profiles. In addition, the endotherm magnitude increases substantially. These phenomena imply potential moisture pick-up by the conventional dispersions and can be a critical quality issue for commercialization. In contrast, there are little changes in DSC profiles of dispersions of the invention. This demonstrates the enhanced stability of dispersion of the invention over conventional dispersions.

Samples of conventional dispersions and dispersions of the invention with 2/1 ratio from before and after the 40° C./75% RH stress tests are further examined under the microscope which vividly revealed the dissolution of water-soluble poloxamer solid particles, and dispersion of water-insoluble ibuprofen solid particles.

Figure 6:
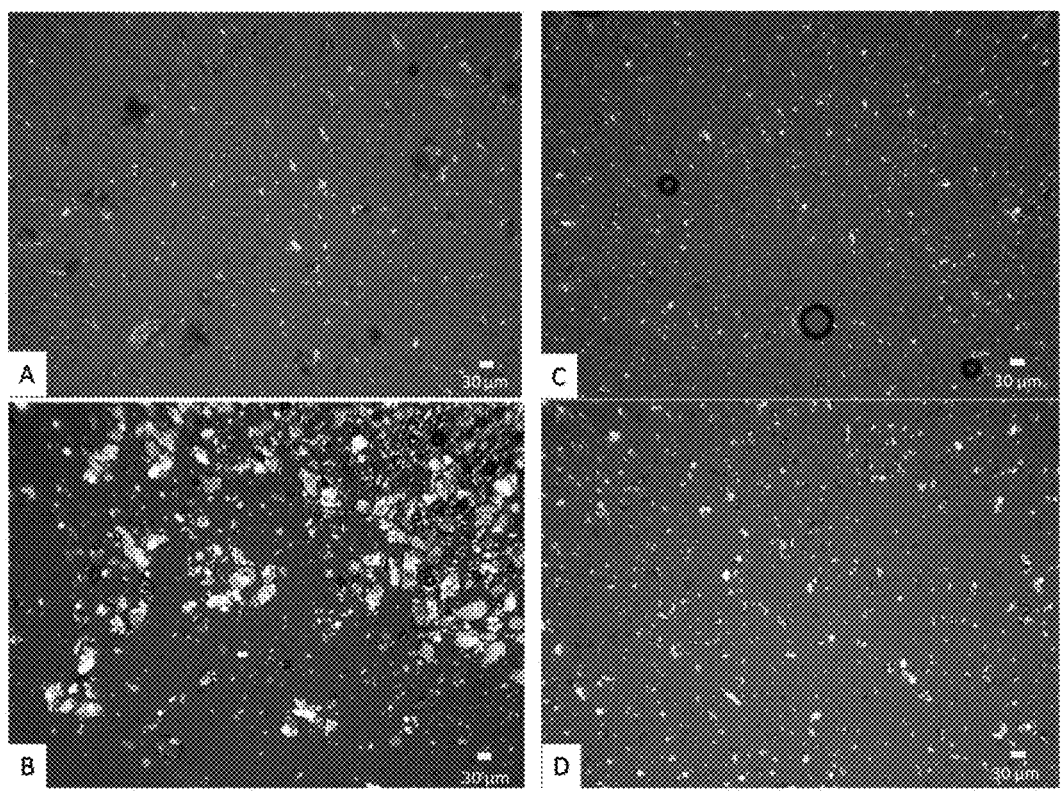
FIG. 6 shows photographs of microscopic view of ibuprofen/poloxamer 188 solid dispersions having w/w ratio of 2/1 before and after stress testing for conventional solid dispersion (photographs A and B, respectively), and hybrid solid dispersion of the invention (photographs C and D, respectively).

Photographs of the microscopic view depicted in FIG. 6 show a noticeable difference in particle size distribution for the conventional dispersion before (photograph A) and after (photograph B) the stability stress testing. The stress tested conventional dispersion shows a significant variation of particle size distribution with presence of large crystals suggesting uncontrolled ibuprofen crystallization during stress testing. For hybrid dispersion samples of the invention, the distribution of crystalline particles before (photograph A) and after (photograph D) stress testing remain quite uniform, the size of all particle remaining less than 30 μm after the stress test. This data supports the conclusion that the API in the hybrid dispersion of the invention undergoes well-controlled crystallization demonstrating uniform distribution of crystalline particles with enhanced physical stability of the dispersion of the invention.

Example 2—Ibuprofen/HPMC (API/Glass-Solution Forming Additive) Solid Dispersions Conventional Glass Solution Solid Dispersion Preparation As listed in Table 4, conventional dispersions of ibuprofen/HPMC (E3 grade) at 1/1, 2/1 and 4/1 w/w ratios were prepared by spray drying process, which is a common procedure to generate glass-solution solid dispersion (Newman, 'Pharmaceutical Amorphous Solid Dispersions', Wiley (2015)). Preliminary screening results showed that the solubility of ibuprofen in HPMC is about 50 wt % of HPMC, i.e. 0.5 part of ibuprofen in 1 part of HPMC w/w. Therefore, these dispersions exceed the solubility limit of ibuprofen in HPMC.

Ibuprofen and HPMC were carefully weighed and dissolved in about 10 grams of methanol/water, 95/5 w/w solvent mixture. The clear solution was vacuum spray dried at 35-40° C. The spray dried particles were stored at ambient temperature in a desiccator.

TABLE 4

Ibuprofen/HPMC Composition of conventional Dispersions

| Ibuprofen/HPMC Ratio, w/w | Ibuprofen (gram) | HPMC (gram) |
|---|---|---|
| 1/1 | 0.5 | 0.5 |
| 2/1 | 0.6 | 0.3 |
| 4/1 | 0.6 | 0.15 |

Preparation of Hybrid Solid Dispersion of the Invention

The composition and ingredients for preparation of samples of the invention employing impinging jet crystallization are shown in Table 5. For the batch stream, ibuprofen and HPMC were carefully weighed and dissolved in methanol/water mixture at 0-5° C. The batch stream solution and water as anti-solvent stream were rapidly mixed via impinging jet mixer and collected in vials at 0-5° C. with magnetic stirring. The resulting slurries were aged for several hours, warmed up to 35-40° C. to re-dissolve a portion of the ibuprofen crystals, and spray-dried under full vacuum at 35-40° C. as described in example 1. The dry particles were removed from the collector and placed at ambient temperature in a desiccator.

TABLE 5

Ibuprofen/HPMC - Composition of Hybrid Dispersions

| Ibuprofen/HPMC (w/w) | Batch Stream | | | | Anti-solvent stream | Temperature (° C.) |
|---|---|---|---|---|---|---|
| | Ibuprofen, (gram) | HPMC, (gram) | MeOH, (gram) | Water, (gram) | Water (gram) | |
| 1/1 | 0.45 | 0.45 | 3 | 0.15 | 4.35 | 0-5 |
| 2/1 | 0.6 | 0.3 | 3 | 0.15 | 4.35 | 0-5 |
| 4/1 | 0.6 | 0.15 | 3 | 0.15 | 4.35 | 0-5 |

Characterization

Samples of conventional dispersions of Table 4 and dispersions of the invention of Table 5 prepared above were examined under the microscope. Microscopic photos of Ibuprofen/HPMC at all weight ratios show similar trend. Only 1/1 and 4/1 weight ratios are shown here to minimize duplication.

Figure 7:
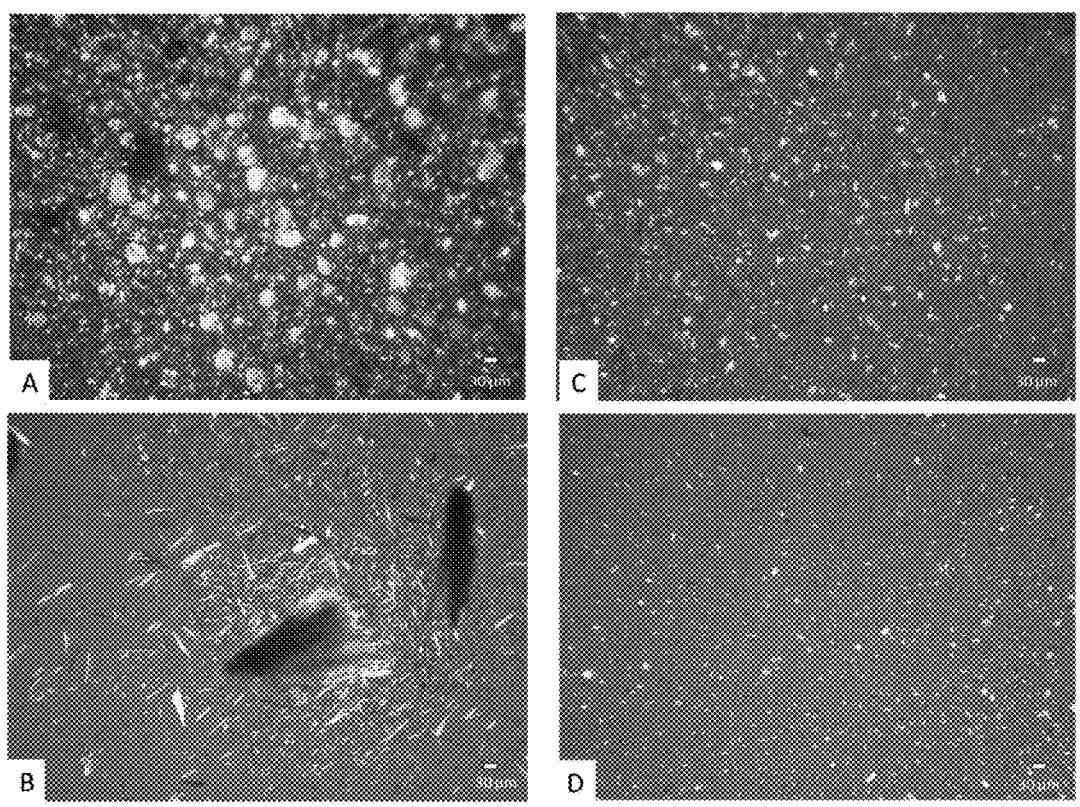
FIG. 7 shows photographs of microscopic view of ibuprofen/HPMC solid dispersions at w/w ratios of 1/1 and 4/1 for conventional solid dispersions (photographs A and B, respectively), and for hybrid solid dispersion of the invention (photographs C and D, respectively).

As shown in FIG. 7, there are noticeable differences in particle size distribution between the conventional dispersion samples and samples of dispersions of the invention. For ibuprofen/HPMC (1/1), the conventional dispersion shows a significant variation of particle size distribution having large particles (photograph A). For ibuprofen/HPMC (4/1), the conventional dispersion shows significant amount of long needle shaped crystals (photograph B). Both suggest uncontrolled crystallization of supersaturated amorphous ibuprofen in the conventional dispersions during storage and water-dispersion for microscopic examination. These observations also vividly reflect the underlying non-uniform distribution of amorphous ibuprofen and water-soluble HPMC additive. In contrast, for the invention's hybrid dispersion samples, the distribution of crystalline particles is quite uniform with all particles having a size of less than 30 µm (photographs C and D). This suggests well controlled crystallization of amorphous ibuprofen in the invention's hybrid dispersion samples during the water dispersion for microscopic examination. These observations clearly reflect the underlying uniformly distributed amorphous ibuprofen, as well water-soluble HPMC additive.

Figure 8:
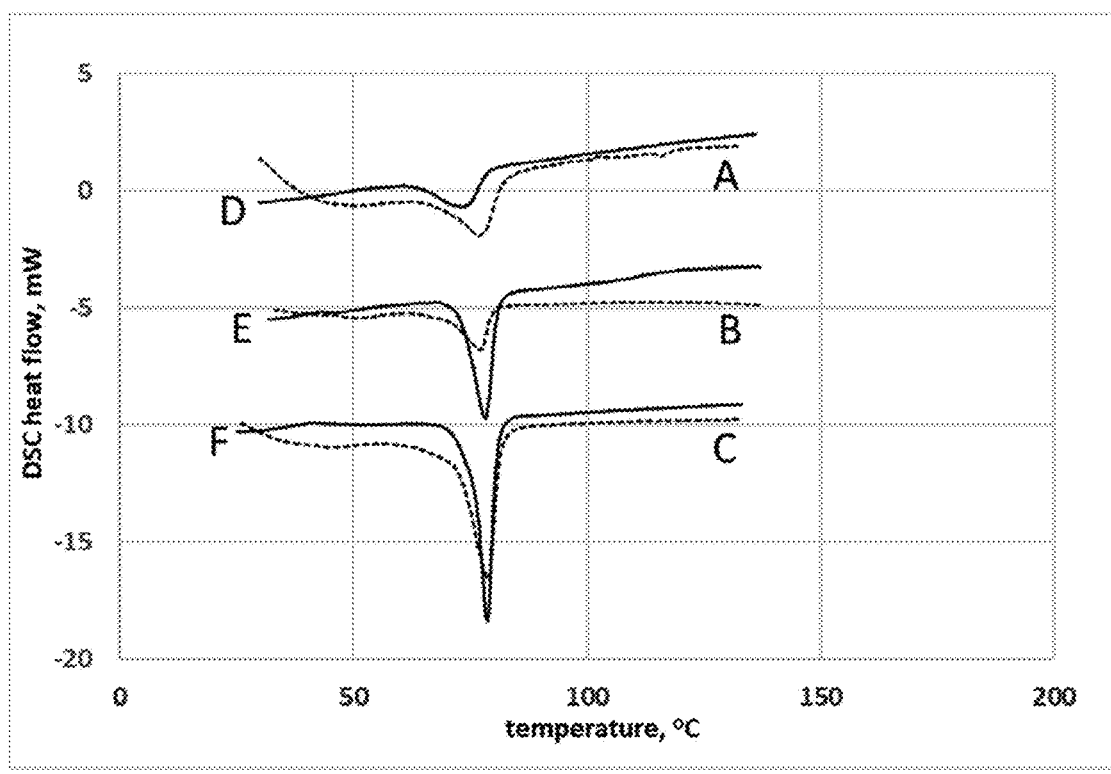
FIG. 8 shows DSC profile of ibuprofen/HPMC solid dispersions at w/w ratios of 1/1, 2/1 and 4/1 for conventional solid dispersions (dotted curves A, B and C, respectively), and for hybrid solid dispersions of the invention (solid curves D, E and F, respectively).

As shown in FIG. 8, DSC profiles of all samples show an endotherm around 75° C., corresponding to the melting of crystalline ibuprofen. Their individual endothermic values and corresponding calculated level of crystalline ibuprofen are listed in Table 6 below:

TABLE 6

Ibuprofen/HPMC Dispersion-Percentage of API in Crystalline-Suspension and Glass-Solution

| Ibuprofen-HPMC ratio & Description | ΔH, Joules/gram | API in Crystalline-Suspension (%) | API in Glass-Solution %) (by Material Balance) |
|---|---|---|---|
| 1/1 conventional glass-solution dispersion, Curve A | ~15 | ~25% | ~75% |
| 1/1 hybrid dispersion, Curve D | ~30 | ~50% | ~50% |
| 2/1 conventional glass-solution dispersion, Curve B | ~25 | ~30% | ~70% |
| 2/1 hybrid dispersion, Curve E | ~65 | ~80% | ~20% |
| 4/1 conventional glass-solution, Curve C | ~40 | ~40% | ~60% |
| 4/1 hybrid dispersion, Curve F | ~90 | ~90% | ~10% |

For the invention's hybrid dispersions, by varying the amount of additive, the percentage of API in crystalline-suspension ranges from 50% to 90% and the percentage of API in glass-solution ranges from 10% to 50% based upon the material balance. The percentage of API in glass-solution is close to the solubility of ibuprofen in the glass-solution forming additive, HPMC. This demonstrates the capability of the invention to vary percentages of API in crystalline-suspension and glass-solution of the hybrid solid dispersion.

For the conventional dispersions, the drug loading exceeds the solubility of ibuprofen in HPMC resulting in a portion of the amorphous ibuprofen to crystallize out from the glass-solution in an uncontrolled manner after the preparation of the conventional dispersion, and the remaining portion of the amorphous ibuprofen remains in supersaturated state, which is unstable over time with or without exposure to moisture.

Dissolution Profile

Figure 9:
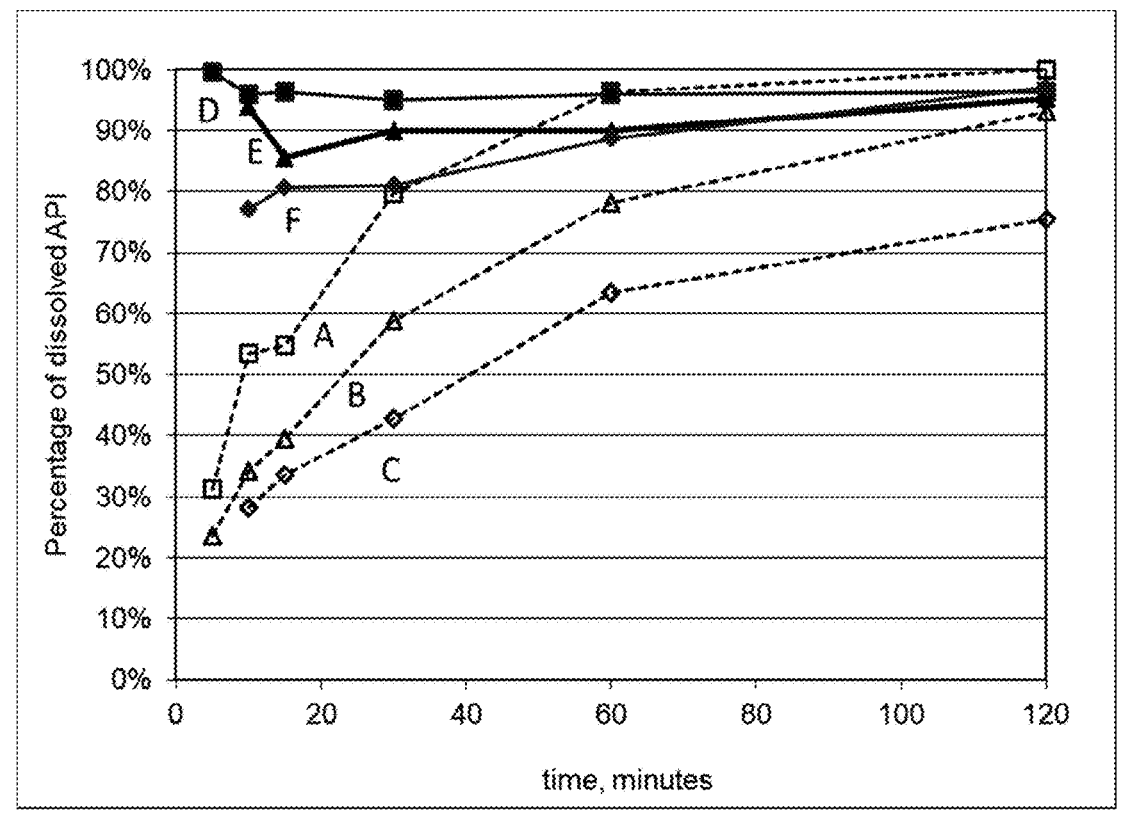
FIG. 9 shows dissolution profiles of ibuprofen/HPMC solid dispersions at w/w ratios of 1/1, 2/1 and 4/1 for conventional solid dispersions (dotted curves A, B and C, respectively), and for hybrid solid dispersions of the invention (curves D, E and F, respectively).

As shown in FIG. 9, the invention's hybrid dispersions exhibit faster dissolution profiles (curves D, E, and F) than those of the conventional dispersions (curves A, B, and C) for all drug loadings. These results highlight the effectiveness of the invention's hybrid solid dispersion in achieving better dissolution profiles than the conventional glass-solution solid dispersions due to the uncontrolled crystallization of API in the latter.

Stability and Drug-Drug/Drug-Excipients Compatibility

To evaluate the drug-drug or drug-excipient compatibility, the conventional and invention's dispersion samples were blended with nicotinamide in an amount equal to the weight of ibuprofen in the dispersion sample. A physical mixture of ibuprofen/HPMC was also blended with nicotinamide. Nicotinamide is chosen as the model drug for the compatibility study because it is known to react with ibuprofen to form ibuprofen-nicotinamide cocrystals. Only results of ibuprofen/HPMC at 2/1 ratio stress tested at 40° C./75% RH for one month are presented here. Samples of ibuprofen/HPMC at 1/1 and 4/1 ratios, stress tested at 30° C./75% RH and 40° C./75% RH respectively, show similar trends, hence, results are not duplicated here.

Figure 10:
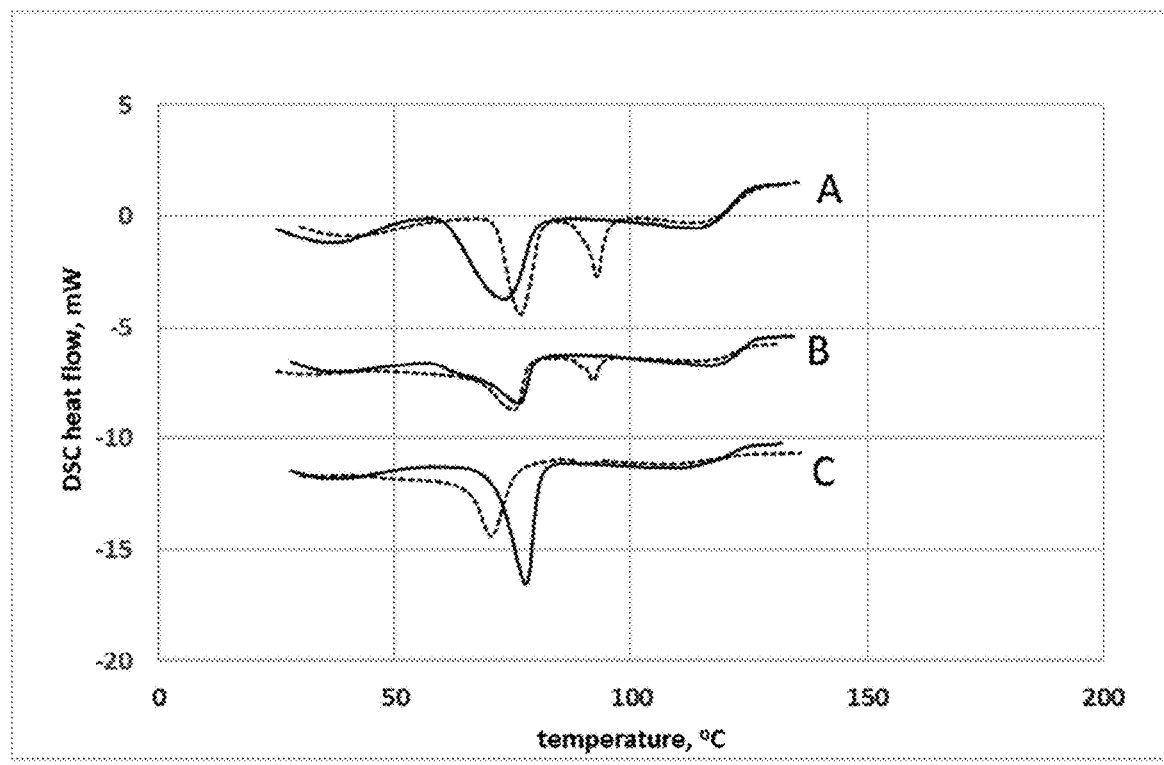
FIG. 10 shows DSC profiles before and after stress testing (solid and dotted lines, respectively), in the presence of nicotinamide, for ibuprofen/HPMC at w/w ratio of 2/1 for a physical mixture (curve A), a conventional solid dispersion (curve B), and a hybrid solid dispersion of the invention (curve C).

FIG. 10 shows DSC profiles before and after stress testing (solid and dotted lines, respectively) for the physical mixture (curve A), the conventional solid dispersion (curve B), and the hybrid solid dispersion (curve C). As shown in FIG. 10, the DSC profile of the physical mixture of ibuprofen, HPMC and nicotinamide, shows an endothermic peak around 70° C. (solid line curve A). This peak is believed to represent melting of ibuprofen. The melting point is depressed due to the presence of nicotinamide. After stress testing, the melting endotherm shifts up to about 75° C. and a new peak around 90° C. appears (dotted line curve A). The new peak corresponds to the melting of the newly formed ibuprofen-nicotinamide co-crystal. The peak shifting behavior and simultaneous appearance of new peak around 90° C. reflects the progress of co-crystallization of ibuprofen with nicotinamide over time. A similar formation of ibuprofen-nicotinamide co-crystal is observed for the conventional dispersion sample (dotted line curve B), but not for the invention's hybrid dispersion sample (dotted line curve C).

Comparing DSC curve behaviors of the physical mixture, the conventional dispersion sample, and the invention's hybrid dispersion sample, the invention's hybrid dispersion shows the least interaction between ibuprofen and nicotinamide. This data demonstrates the enhanced drug-drug and drug-excipient compatibility of the invention's hybrid solid dispersions.

Example 3—Ibuprofen/HPMC/Poloxamer (API/Glass-Solution Forming Additive/Eutectic-Mixture Forming Additive) Solid Dispersions Conventional Solid Dispersion Preparation Conventional dispersions of ibuprofen with HPMC (E3 grade) and poloxamer 407 as additives as listed in Table 7 were prepared using Park et al. (Arch Pharm. Res., 32, p 767 (2009); Arch. Pharm. Res., 33, p 1217 (2010)) procedure. HPMC is the glass-solution forming additive and poloxamer 407 is the eutectic-mixture forming additive.

TABLE 7

Ibuprofen/HPMC/poloxamer 407-Composition of Conventional dispersions

| Ibuprofen/ HPMC/ poloxamer w/w/w | Ibuprofen (gram) | HPMC (gram) | poloxamer 407 (gram) | Water (gram) | Temperature (° C.) |
|---|---|---|---|---|---|
| 2/0.8/0.2 | 0.4 | 0.16 | 0.04 | 2.5 | 20-25 |
| 4/0.8/0.2 | 0.8 | 0.16 | 0.04 | 2.5 | 20-25 |
| 9/0.8/0.2 | 0.9 | 0.08 | 0.02 | 5 | 20-25 |

Ibuprofen was sieved through a mesh #60 screen (250 μm opening) first. The sieved ibuprofen, HPMC and poloxamer 407 were carefully weighed and charged into vials containing water. The aqueous slurry was dispersed with a vortex mixer vigorously for at least 5 to 10 minutes. The slurry was spread over a glass tray in a thin film and dried under full vacuum at ambient temperature. The dry solid particles were collected from the tray and stored at ambient temperature in a desiccator.

Preparation of Hybrid Solid Dispersion of the Invention

The invention samples, as listed in Table 8, were prepared by using impinging jet crystallization. Ibuprofen, HPMC and poloxamer 407 were carefully weighed and dissolved in methanol/water mixture at 0-5° C. The batch and the antisolvent water were rapidly mixed via an impinging jet mixer and collected in a vial at 0-5° C. with magnetic stirring for several hours. Then the slurries were warmed up to 35 to 40° C., and spray-dried under full vacuum at 35 to 40° C. to generate dry solid particles. The dry particles were placed at ambient temperature in a desiccator.

TABLE 8

Ibuprofen/HPMC/poloxamer 407 - Composition of Invention's Hybrid Dispersions

| Ibuprofen/ HPMC/ Poloxamer ratio (w/w/w) | Batch Stream | | | | | Antisolvent stream | |
|---|---|---|---|---|---|---|---|
| | Ibuprofen (gram) | HPMC (gram) | Poloxamer 407 (gram) | MeOH (gram) | Water (gram) | Water (gram) | Temperature (° C.) |
| 2/0.8/0.2 | 0.4 | 0.16 | 0.04 | 2 | 0.1 | 2.9 | 0-5 |
| 4/0.8/0.2 | 0.4 | 0.08 | 0.02 | 2 | 0.1 | 2.9 | 0-5 |
| 9/0.8/0.2 | 0.9 | 0.08 | 0.02 | 4.2 | 0.2 | 2.8 | 0-5 |

Characterization

Figure 11:
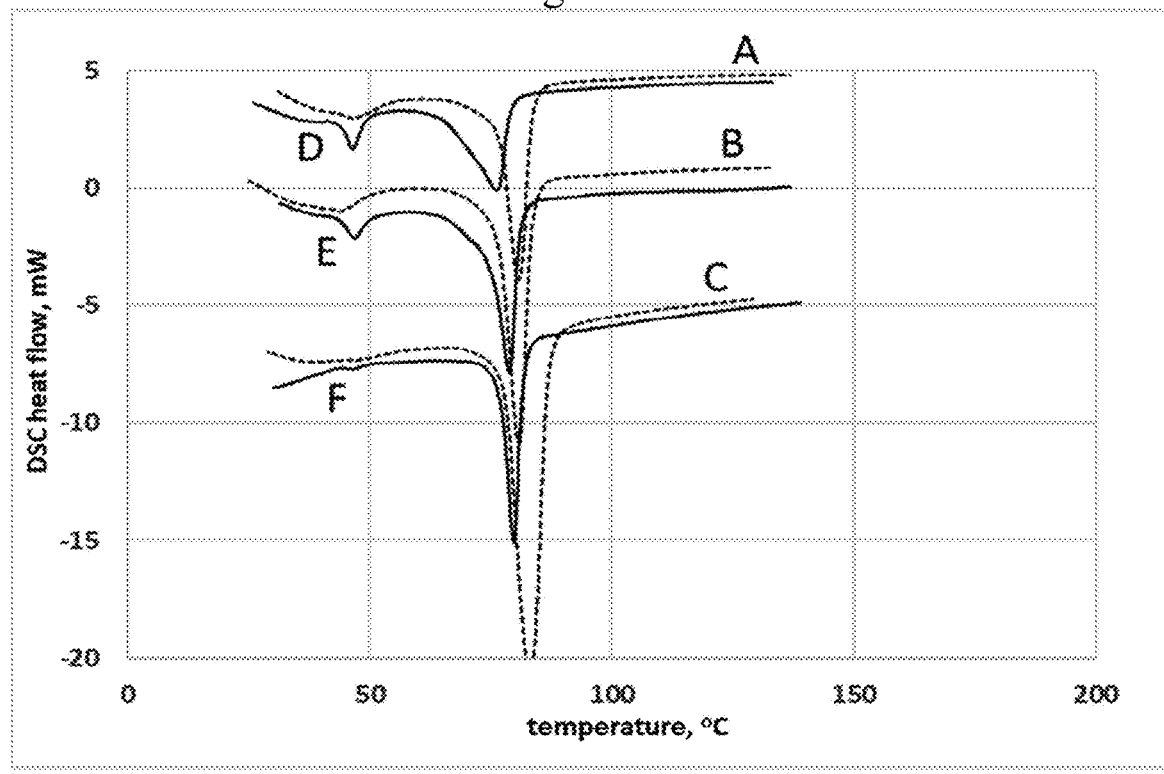
FIG. 11 shows DSC profile for ibuprofen/HPMC/poloxamer 407 solid dispersions at w/w ratios of 2/0.8/0.2, 4/0.8/0.2 and 9/0.8/0.2 for conventional solid dispersions (dotted curves A, B and C, respectively), and hybrid solid dispersions of the invention (curves D, E and F, respectively).

As shown in FIG. 11, DSC profiles of all samples show an endotherm or trough around 50° C., corresponding to the melting of ibuprofen/poloxamer 407 eutectic-mixture, and an endotherm around 70 to 75° C., corresponding to melting of crystalline ibuprofen. One key difference between the conventional and invention's dispersion samples is a clear endothermic peak of eutectic-mixture melting at about 50° C. in case of the samples of the invention's dispersions (curves D, E and F) and a broad trough in the baseline in case of the conventional dispersions (curves A, B and C). For the invention's dispersion of 9/0.8/0.2, the eutectic-mixture melting peak is small, but its presence is clearly noticeable. Also, there is more depression of melting point of ibuprofen (to about 70° C.) in case of the invention's samples than for the conventional dispersions (to about 75° C.). These two concurrent thermal behaviors suggest a closer contact among the ibuprofen and poloxamer crystals and more uniform distribution in case of the invention's hybrid dispersion samples.

The individual endothermic values and corresponding calculated levels of ibuprofen in crystalline-suspension, glass-solution and eutectic-mixture are listed in Table 9.

those of the conventional dispersions (curves A, B and C) at all drug loadings. These results again highlight the advantages of the invention over the current existing technology.

Stability

Figure 13:
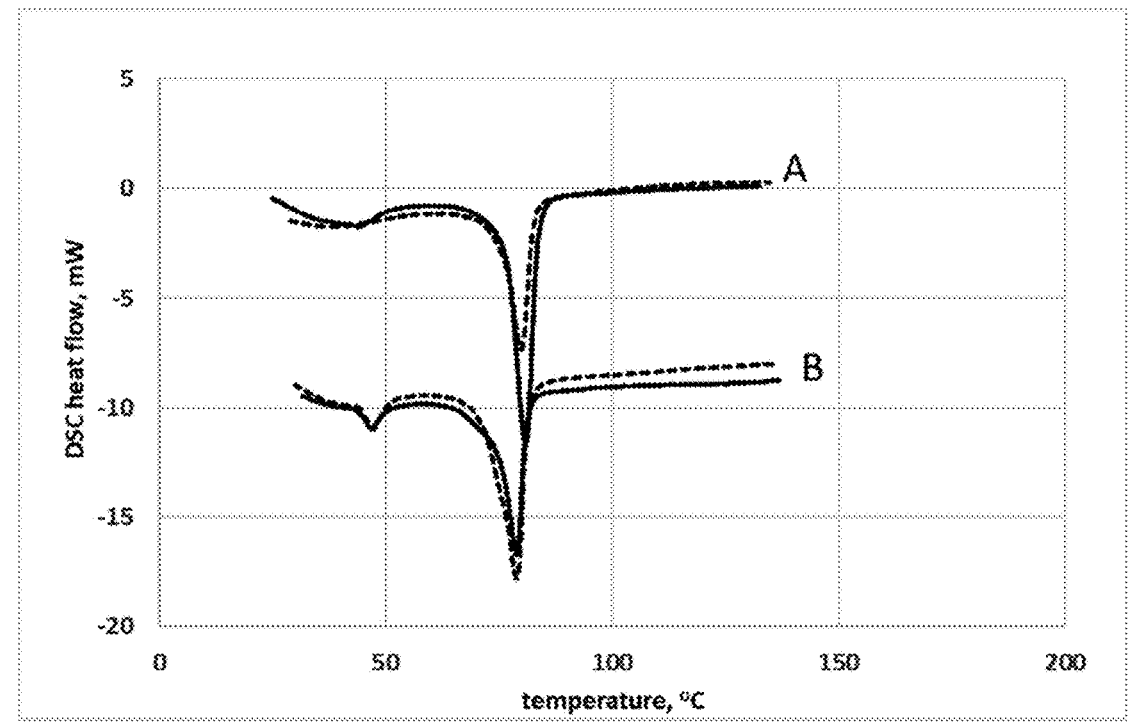
FIG. 13 shows DSC profiles before and after stress testing (solid and dotted lines, respectively) for ibuprofen/HPMC/poloxamer 407 at ratio 4/0.8/0.2 for conventional solid dispersion (curve A), and hybrid solid dispersion of the invention (curve B).

Conventional and hybrid dispersion samples were stored in open vials at the 40° C./75% RH for one month. Results of 4/0.8/0.2 weight ratio are presented in FIG. 13. Results of 2/0.8/0.2 and 9/0.8/0.2 weight ratio system are similar and not duplicated here. As shown in the figure, all samples show excellent stability. The stability of conventional dispersion (dotted line curve A) is fully expected due to its predominant crystalline nature. However, the invention's hybrid solid dispersion also exhibits similar stability (dotted line curve B), despite the presence of significant amount of amorphous API. This data again confirms the excellent stability of invention's hybrid solid dispersions.

Example 4—Ibuprofen Sodium/Ibuprofen/Eudragit/Poloxamer 407 and Ibuprofen Sodium/Ibuprofen/PMC/Poloxamer 407 (API Salt/API/Glass-Solution Forming Additive/Eutectic-Mixture Forming Additive) Solid Dispersions Ibuprofen is a free acid which can react with sodium hydroxide to form the sodium salt of ibuprofen. In compari-

TABLE 9

Ibuprofen-HPMC-poloxamer 407 System-Percentage of Crystalline-suspension, Eutectic-mixture and Glass-solution

| Ibuprofen/HPMC/ Poloxamer Ratio & Description | ΔH, Joules/gram about 50° C. | API in Eutectic-mixture (%) | ΔH, Joules/gram about 70° C.-75° C. | API in Crystalline-suspension (%) | API in Glass-solution (%) (by material balance) |
|---|---|---|---|---|---|
| 2/0.8/0.2 conventional dispersion, Curve A | broad trough | N/A | ~75 | 95% or higher | N/A |
| 2/0.8/0.2 invention's hybrid dispersion, Curve D | ~7 | ~10% | ~55 | ~70% | ~20% |
| 4/0.8/0.2 conventional dispersion, Curve B | broad trough | N/A | ~90 | 95% or higher | N/A |
| 4/0.8/0.2 invention's hybrid dispersion, Curve E | ~4 | ~5% | ~65 | ~70% | ~25% |
| 9/0.8/0.2 conventional dispersion, Curve C | Broad trough | N/A | ~100 | 95% or higher | N/A |
| 9/0.8/0.2 invention's hybrid dispersion, Curve F | Less than 1 | Less than 1% | ~90 | ~85% | ~15% |

For both invention samples, the percentage of ibuprofen dispersed in crystalline suspension is 70% to 85% with variation of ibuprofen percentages in the eutectic-mixture and glass-solution. For the conventional dispersions, API exists predominantly in crystalline-suspension at about 95% or higher with less than 5% of API in glass-solution and eutectic-mixture.

Both the conventional and the invention's dispersion samples have the same composition (ingredients). But Table 9 data shows that the distribution of API is appreciably different between the conventional and the invention's samples. These results highlight that the crystallization/drying procedure for the preparation of the dispersion, for example amount of dissolved API in the solvent mixture, can be an additional variable to adjust the API distribution in the hybrid solid dispersion, besides the composition of the ingredients.

Dissolution Profile

Figure 12:
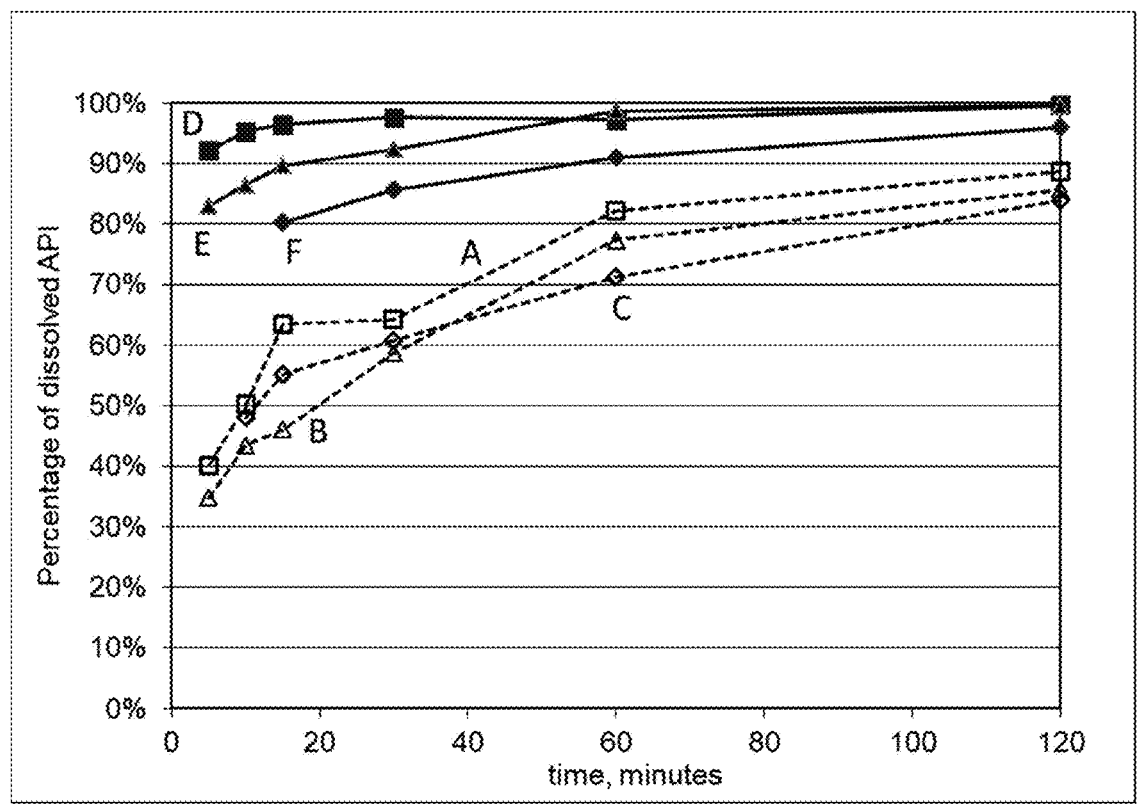
FIG. 12 shows dissolution profile of ibuprofen/HPMC/poloxamer 407 solid dispersions at w/w ratios of 2/0.8/0.2, 4/0.8/0.2 and 9/0.8/0.2 for conventional solid dispersions (dotted curves A, B, and C, respectively), and for hybrid solid dispersions of the invention (solid curves D, E and F, respectively).

FIG. 12 shows that the dispersions of the invention exhibit more rapid dissolution profiles (curves D, E and F) than son to ibuprofen which has a low aqueous solubility, ibuprofen sodium has a high aqueous solubility. However, the salt is hygroscopic and can absorb moisture to form the dihydrate. The dihydrate salt can be dehydrated and converted back to anhydrate under low humidity. A hybrid solid dispersion combining ibuprofen sodium, which may exist in dihydrate or anhydrate forms, and ibuprofen is exemplified here to demonstrate the applicability of the invention to incorporate APIs in different chemical and physical forms.

Physical Mixture Preparation as Comparative Example

As shown in Table 10, comparative samples consist of physical mixtures of ibuprofen sodium and ibuprofen as APIs, and Eudragit EPO, HPMC (E3 grade), and poloxamer 407 as additives. Water-insoluble Eudragit EPO and water-soluble HPMC are the glass-solution forming additive and poloxamer 407 is the eutectic-mixture forming additive. Conventional dispersions could not be prepared in this case because no prior literature describing such dispersions could be found. All solids were sieved through a mesh #60 screen (250 μm opening) first. Ibuprofen-Na-sait, ibuprofen, Eudragit, HPMC and poloxamer 407 were carefully weighed and physically mixed in a vial with vortex mixture for least 5 to 10 minutes. The physical mixture samples are stored at ambient temperature in a desiccator.

TABLE 10

Ibuprofen Sodium/Ibuprofen-Composition of Physical Mixtures and Invention's Dispersions

| Ibuprofen sodium/ Ibuprofen/ Polymer/ poloxamer 407 ratio (w/w) | Ibuprofen Sodium salt (mg) | Ibuprofen (mg) | Eudragit EPO (mg) | HPMC, (mg) | Poloxamer 407 (mg) |
|---|---|---|---|---|---|
| 1.5/0.5/0.5/0.5 | 150 | 50 | 50 | 0 | 50 |
| 1.75/0.25/0.25/02.5 | 175 | 25 | 25 | 0 | 25 |
| 1.5/0.5/0.5/0.5 | 150 | 50 | 0 | 50 | 50 |
| 1.75/0.25/0.25/0.25 | 175 | 25 | 0 | 25 | 25 |

Preparation of Hybrid Solid Dispersions of the Invention

The invention's samples were prepared with the same composition as those for the physical mixtures. For invention samples containing Eudragit, 2 to 2.5 volumes of acetone (with respect to the total amount of ingredients) were added to the physical mixture. For samples containing HPMC, 2-2.5 volumes of acetone/water 95/5 w/w solvent mixture were charged to the physical mixture. Solubility of ibuprofen sodium in pure acetone or acetone/water 95/5 is estimated to be less than 1% of the total ibuprofen sodium added. All other ingredients including ibuprofen, Eudragit, HPMC and poloxamer 407 are soluble in acetone or 95/5 acetone/water mixture. The resulting slurries were vortex-mixed overnight and the slurries were vacuum dried in a tray dryer at 35 to 40° C. After vacuum drying, all solids were stored at ambient temperature in a desiccator.

Characterization

Figure 14:
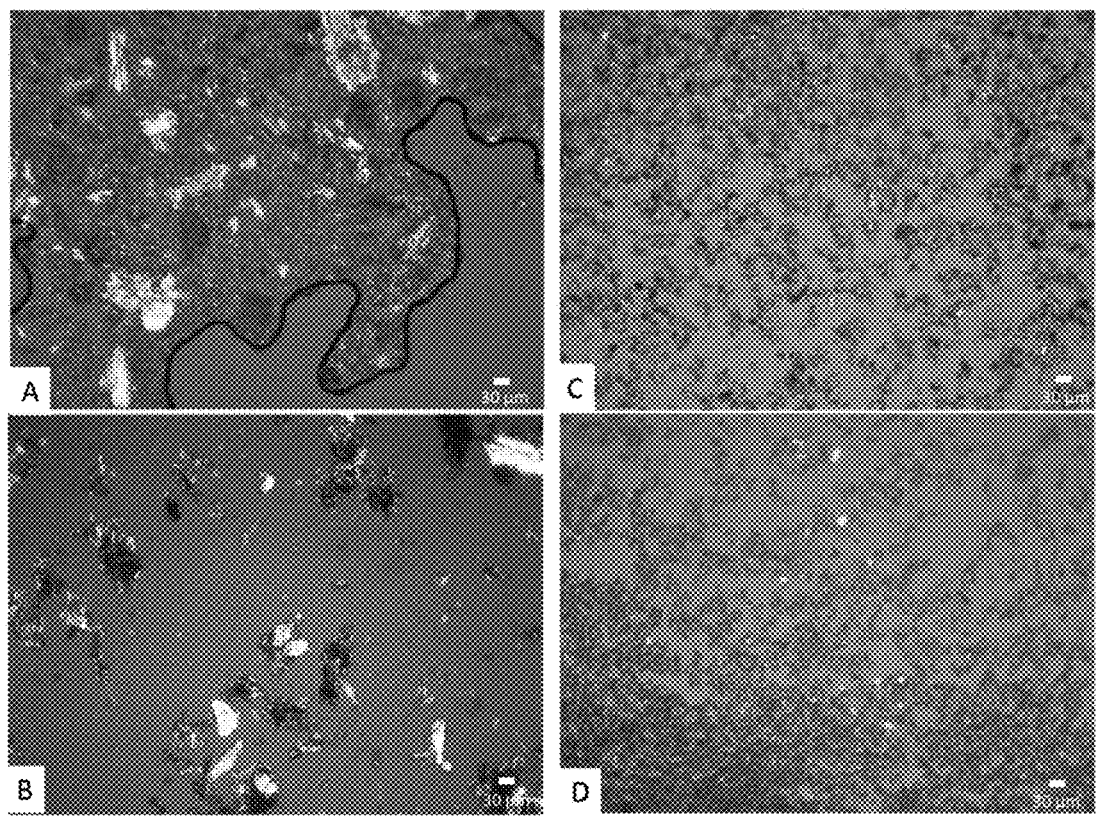
FIG. 14 shows microscopic view for ibuprofen sodium/ibuprofen/Eudragit/poloxamer having ratios 1.5/0.5/0.5/0.5 and 1.75/0.25/0.5/0.5 for physical mixtures (photographs A and B, respectively), and hybrid solid dispersion of the invention (photographs A and B, respectively).

Slightly modifying the law et al. protocol described above, a pinch of dry solid particles is dispersed with acetone, instead of water, on the microscope slides. FIG. 14 shows photographs of the microscopic view obtained for ibuprofen sodium/ibuprofen/Eudragit/poloxamer ratios 1.5/0.5/0.5/0.5 and 1.75/0.25/0.5/0.5 for the physical mixtures (photographs A and B, respectively) and the hybrid dispersions (photographs C and D, respectively). As shown, the physical mixtures exhibit significant level of agglomerates. On the other hand, the dispersions of the invention show well dispersed ibuprofen sodium particles where all particles have a size of less than 30 μm. Similar behaviors are observed for the HPMC system and are not duplicated here. These observations demonstrate the uniform distribution of crystalline ibuprofen sodium particles in the hybrid dispersion.

Figure 15:
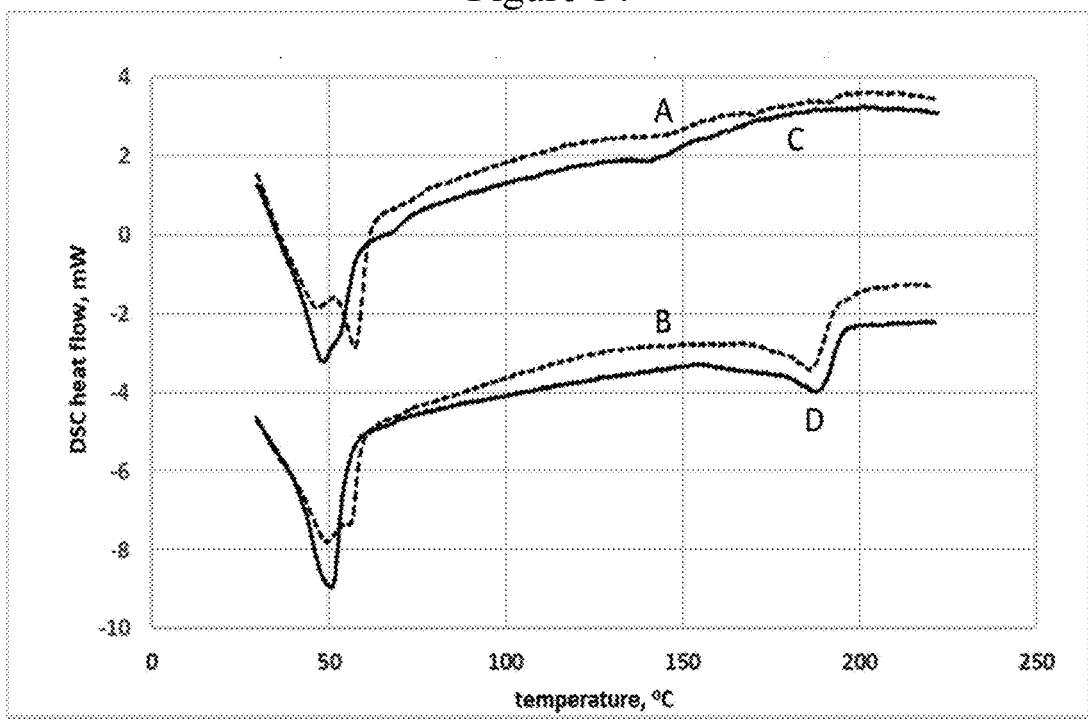
FIG. 15 shows dotted curves A and B depicting the DSC profiles of physical mixtures having ibuprofen sodium/ibuprofen/Eudragit/poloxamer ratios of 1.5/0.5/0.5/0.5 and 1.75/0.25/0.5/0.5, respectively, and solid curves C and D depicting the DSC profiles of hybrid solid dispersions of the invention having ibuprofen sodium/ibuprofen/Eudragit/poloxamer ratios of 1.5/0.5/0.5/0.5 and 1.75/0.25/0.5/0.5, respectively.

FIG. 15 shows the DSC profiles of ibuprofen sodium/ibuprofen/Eudragit/poloxamer ratios 1.5/0.5/0.5/0.5 and 1.75/0.25/0.5/0.5 for the physical mixtures (curves A and B, respectively) and the hybrid dispersions (curves C and D, respectively). The melting endotherm around 50° C. reflects the melting of eutectic-mixture of ibuprofen and poloxamer 407. The endotherm around 60° C. reflects the melting of poloxamer 407, and the endotherm around 185° C. to 200° C. reflects the melting of ibuprofen sodium. Similar behaviors are observed for the HPMC system and are not duplicated here.

For the physical mixtures, the DSC curves show two overlapping melting endotherms corresponding to the eutectic-mixture and poloxamer, respectively. For the invention samples, the DSC curves show primarily one melting endotherm corresponding to the eutectic-mixture. This difference suggests a closer contact between ibuprofen and poloxamer crystals and their uniform distribution within the invention's hybrid dispersion in comparison to physical mixtures. Above 50° C., the DSC profiles of control and invention samples show continuous release of heat and are quite similar. It is noted that melting endotherm of ibuprofen sodium is not observed at a lower drug loading (ibuprofen sodium/ibuprofen/Eudragit/poloxamer ratio 1.5/0.5/0.5/0.5, curves A and C) suggesting a complete dissolution of ibuprofen sodium with ibuprofen or additives upon heating during the thermal analysis.

Since the thermal behavior of comparative and invention's samples above 50° C. are very similar, the data supports the conclusion that the ibuprofen sodium percentage in the crystalline-suspension of the hybrid dispersion of the invention is close to that of the physical mixture. That is, for 1.5/0.5/0.5/0.5 ratio, 75% of API exists in the crystalline-suspension and 25% remaining API exists in eutectic-mixture and glass-solution in the hybrid dispersion of the invention. For 1.75/0.25/0.25/0.25 ratio, 87.5% of API exists in the crystalline-suspension and 12.5% remaining API exists in eutectic-mixture and glass-solution in the hybrid dispersion of the invention. This demonstrates the capability of the invention to control the API percentage and distribution at different chemical & physical forms.

Dissolution Behavior

Figure 16:
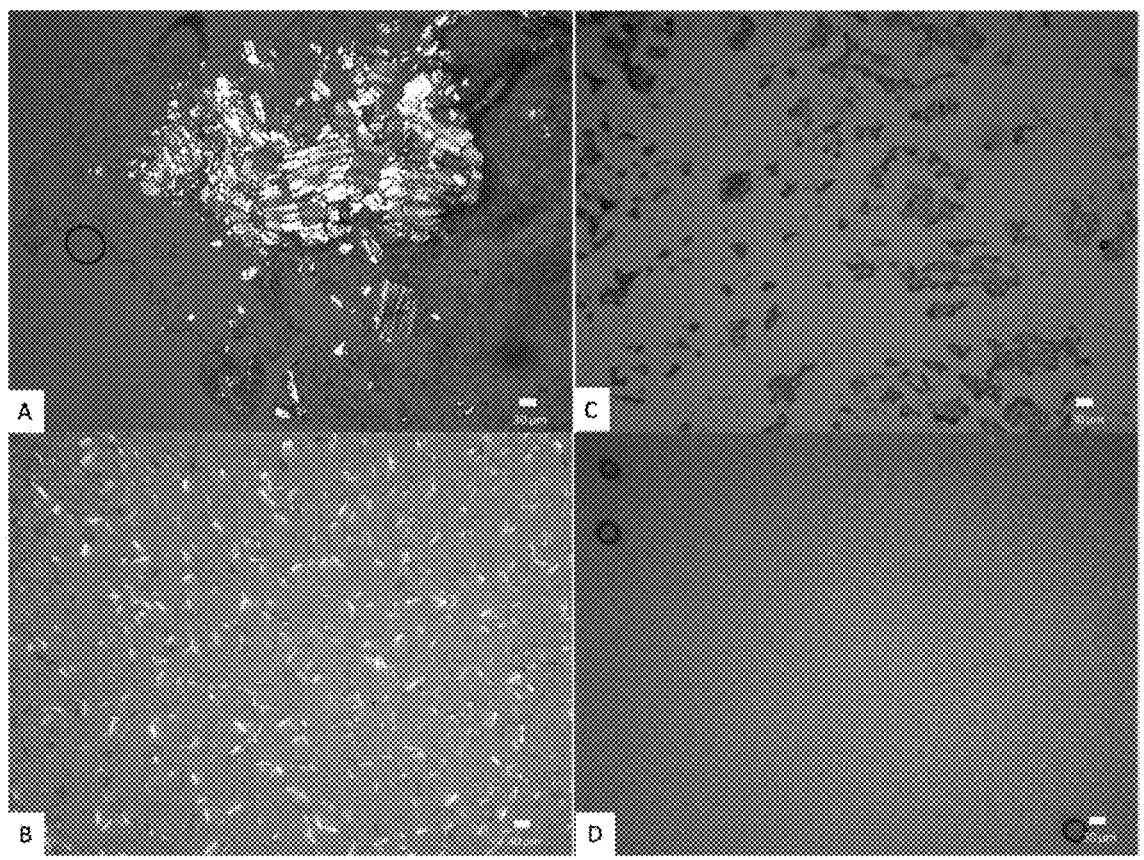
FIG. 16 shows microscopic view of recrystallization behavior after dissolution for ibuprofen sodium/ibuprofen/Eudragit/poloxamer at ratio of 1.5/0.5/0.5/0.5 for a physical mixture (photograph A), and the hybrid solid dispersion of the invention (photograph C), and also for ibuprofen sodium/ibuprofen/HPMC/poloxamer at ratio of 1.5/0.5/0.5/0.5 for a physical mixture (photograph B), and the hybrid solid dispersion of the invention (photograph D).

Because ibuprofen sodium is highly water-soluble, the dissolution protocol is substituted by the protocol for viewing particles under the microscope for monitoring the particle dissolution behavior. A pinch of dry solid particles is dispersed with water on the microscope slide to explore the dissolution behavior of solid particles. Microscopic photographs of 1.5/0.5/0.5/0.5 ratio for both Eudragit and HPMC samples are shown in FIG. 16. Similar trends were observed for the 1.75/0.25/0.25/0.25 compositions, which are not duplicated here.

For the physical mixtures, an appreciable level of ibuprofen crystals was observed after the dissolution of ibuprofen sodium (photographs A and B). In contrast, for the invention's hybrid dispersion samples, no ibuprofen crystals were observed (photographs C and D). For the physical mixture with Eudragit additive, additional irregular-shaped amorphous Eudragit particles were noted (photograph A). For the dispersion of the invention with Eudragit additive, amorphous Eudragit particles were observed (photograph C). These observations suggest that the invention's hybrid solid dispersion can maintain metastability of supersaturated API solution better than physical mixtures. For solid dispersion, better metastability of supersaturation solutions generally leads to better bioavailability.

Stability and Hygroscopicity

To compare the hygroscopicity of solid particles, physical mixtures samples and the invention's hybrid dispersion samples of ibuprofen sodium/ibuprofen/Eudragit/poloxamer were chosen. Samples of comparable weight were placed in polypropylene vials with open cap and dried in desiccator under vacuum over a week to ensure no residual moisture existed. These vials were then quickly closed with caps, weighed and stored in 40° C./75% RH stability chamber for a month. Water vapor can permeate through the polypropylene vial wall and can be absorbed by the solid particles within the vials.

Figure 17:
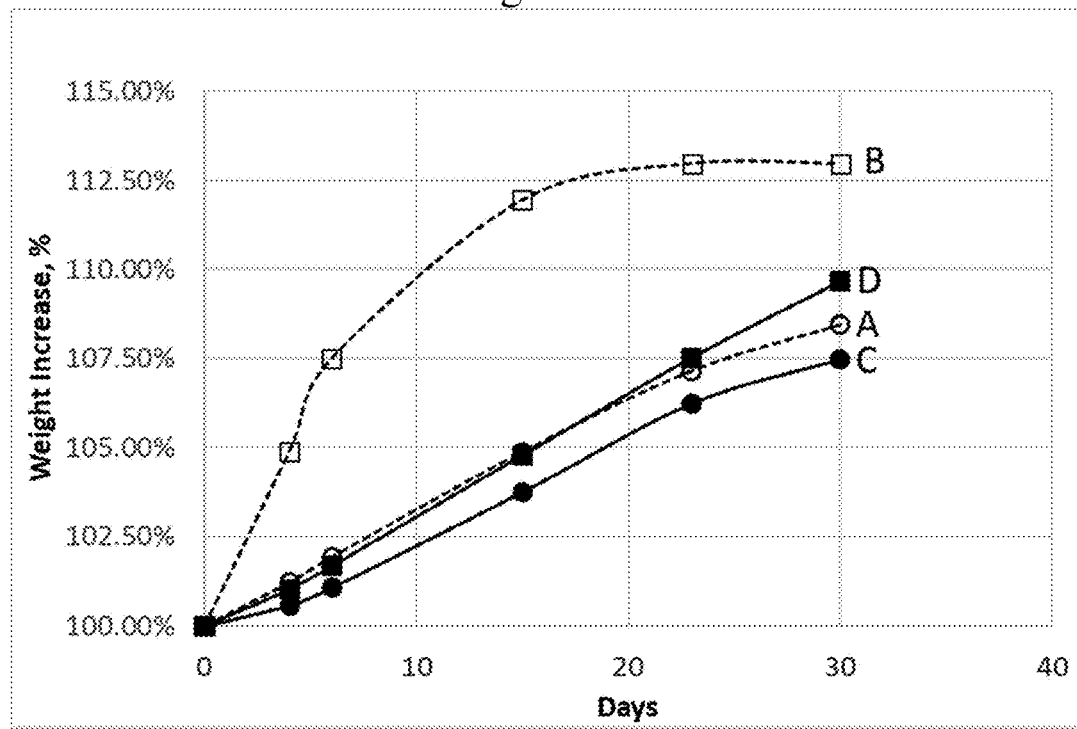
FIG. 17 shows the weight change profiles, resulting from water absorption, for ibuprofen sodium/ibuprofen/Eudragit/poloxamer ratios of 1.5/0.5/0.5/0.5 and 1.75/0.25/0.5/0.5 for physical mixtures (dotted curves A and B, respectively), and for hybrid solid dispersions of the invention (solid curves C and D, respectively).

FIG. 17 plots the weight change profiles of the samples. These profiles show a significant slower water absorption rate for the invention samples (solid curves C and D) than those of the physical mixtures (dotted curves A and B). At a higher drug loading of 1.75/0.25/0.25/0.25, the physical mixture reached a plateau of about 13% weight increase at day 15 (curve B) indicating that all ibuprofen sodium anhydrate had converted to ibuprofen sodium dihydrate at day 15. But the dispersion of the invention did not reach the plateau even at day 30 (curve D). At a lower drug loading of 1.5/0.5/0.5/0.5, neither the physical mixture (curve A) nor the hybrid of the invention (curve C) reached the plateau. The amount of water absorbed by the dispersion of the invention was slower by about 5 days than that of the physical mixture under the 40° C./75% RH conditions.

In general, moisture can have a significant negative impact on drug-drug & drug-excipient interaction, drug shelf life and microbiological burden. These data demonstrate the enhanced chemical and physical stability of invention's hybrid solid dispersions.

The invention claimed is:

1. A pharmaceutical composition comprising:
    an active pharmaceutical ingredient; and
    pharmaceutically acceptable glass-solution forming additives, and/or
    pharmaceutically acceptable eutectic-mixture forming additives,
wherein the active pharmaceutical ingredient and the pharmaceutically acceptable additives are present in the form of a hybrid solid dispersion consisting of a uniformly distributed solid dispersion of:
    a crystalline-suspension; and
    a glass-solution and/or a eutectic-mixture,
wherein the active pharmaceutical ingredient is present in an amount of from more than 50% w/w to about 90% w/w with respect to the total amount of the active pharmaceutical ingredient and the pharmaceutically acceptable glass-solution forming and/or eutectic-mixture forming additives in the pharmaceutical composition,
wherein about 50% w/w to about 95% w/w of the active pharmaceutical ingredient is dispersed in the crystalline-suspension and the remaining active pharmaceutical ingredient is dispersed in the glass-solution and/or the eutectic-mixture,
wherein crystalline active pharmaceutical ingredient exists in a nano/micro particle size range and is uniformly distributed in the hybrid solid dispersion, and
wherein amorphous active pharmaceutical ingredient, when present, is uniformly distributed in the hybrid solid dispersion,
wherein the composition is prepared by a process comprising:
    i) generating a uniform suspension of nano/micro size particles of the active pharmaceutical ingredient's crystals in one or more solvents containing partially dissolved active pharmaceutical ingredient and fully dissolved pharmaceutically acceptable glass-solution forming and/or eutectic-mixture forming additives; and
    ii) evaporating the solvents from the suspension to obtain dry solid particles.

2. A pharmaceutical composition consisting essentially of:
    an active pharmaceutical ingredient; and
    pharmaceutically acceptable glass-solution forming additives, and/or
    pharmaceutically acceptable eutectic-mixture forming additives,
wherein the active pharmaceutical ingredient and the pharmaceutically acceptable additives are present in the form of a hybrid solid dispersion consisting of a uniformly distributed solid dispersion of:
    a crystalline-suspension; and
    a glass-solution and/or a eutectic-mixture,
wherein the active pharmaceutical ingredient is present in an amount of from more than 50% w/w to about 90% w/w with respect to the total amount of the active pharmaceutical ingredient and the pharmaceutically acceptable glass-solution forming and/or eutectic-mixture forming additives in the pharmaceutical composition,
wherein about 50% w/w to about 95% w/w of the active pharmaceutical ingredient is dispersed in the crystalline-suspension and the remaining active pharmaceutical ingredient is dispersed in the glass-solution and/or the eutectic-mixture,
wherein crystalline active pharmaceutical ingredient exists in a nano/micro particle size range and is uniformly distributed in the hybrid solid dispersion, and wherein amorphous active pharmaceutical ingredient, when present, is uniformly distributed in the hybrid solid dispersion,
wherein the composition is prepared by a process comprising:
    i) generating a uniform suspension of nano/micro size particles of the active pharmaceutical ingredient's crystals in one or more solvents containing partially dissolved active pharmaceutical ingredient and fully dissolved pharmaceutically acceptable glass-solution forming and/or eutectic-mixture forming additives; and
    ii) evaporating the solvents from the suspension to obtain dry solid particles.

3. The composition according to claim 1, wherein about 50% w/w to about 90% w/w of the active pharmaceutical ingredient is dispersed in the crystalline-suspension and the remaining active pharmaceutical ingredient is dispersed in the glass-solution and/or the eutectic-mixture.

4. The composition according to claim 1, wherein the active pharmaceutical ingredient exists in different chemical and/or physical forms in the crystalline-suspension, the glass-solution and/or the eutectic-mixture.

5. The composition according to claim 1, wherein the active pharmaceutical ingredient is ibuprofen, and/or ibuprofen sodium.

6. The composition according to claim 1, wherein the composition further comprises one or more additional active pharmaceutical ingredients.

7. A process for the preparation of a pharmaceutical composition comprising:
    an active pharmaceutical ingredient; and
    pharmaceutically acceptable glass-solution forming additives, and/or
    pharmaceutically acceptable eutectic-mixture forming additives,
wherein the active pharmaceutical ingredient and the pharmaceutically acceptable additives are present in the form of a hybrid solid dispersion consisting of a uniformly distributed solid dispersion of:
    a crystalline-suspension; and
    a glass-solution and/or a eutectic-mixture,
wherein the active pharmaceutical ingredient is present in an amount of from more than 50% w/w to about 90% w/w with respect to the total amount of the active pharmaceutical ingredient and the pharmaceutically acceptable glass-solution forming and/or eutectic-mixture forming additives in the pharmaceutical composition, wherein about 50% w/w to about 95% w/w of the active pharmaceutical ingredient is dispersed in the crystalline-suspension and the remaining active pharmaceutical ingredient is dispersed in the glass-solution and/or the eutectic-mixture,
wherein crystalline active pharmaceutical ingredient exists in a nano/micro particle size range and is uniformly distributed in the hybrid solid dispersion, and
wherein amorphous active pharmaceutical ingredient, when present, is uniformly distributed in the hybrid solid dispersion,
wherein the process comprises:
  i) generating a uniform suspension of nano/micro size particles of the active pharmaceutical ingredient's crystals in one or more solvents containing partially dissolved active pharmaceutical ingredient and fully dissolved pharmaceutically acceptable glass-solution forming and/or eutectic-mixture forming additives; and
  ii) evaporating the solvents from the suspension to obtain dry solid particles,
wherein the active pharmaceutical ingredient is present in an amount of from more than 50% w/w to about 90% w/w with respect to the total amount of the active pharmaceutical ingredient and the pharmaceutically acceptable glass-solution forming and/or eutectic-mixture forming additives, and wherein at least about 50% w/w of the active pharmaceutical ingredient is undissolved and at least about 5% w/w of the active pharmaceutical ingredient is in dissolved form.

8. The process of claim 7, wherein the uniform suspension is generated by dissolving the active pharmaceutical ingredient in one or more solvents and then at least partially crystallizing out the active pharmaceutical ingredient from the solvents.

9. The process of claim 7, wherein the uniform suspension is generated by mixing the active pharmaceutical ingredient crystals and one or more solvents to form a slurry or wet mass.

10. The process of claim 7, wherein the evaporation is performed by a batch process.

11. The process of claim 7, wherein the uniform suspension is placed in a dryer and the solvent or solvents are evaporated.

12. The process of claim 7, wherein the evaporation is performed by a continuous process.

13. The process of claims 7, wherein the uniform suspension is continuously fed into a dryer as a stream and the solvents are evaporated.

14. The process of claim 7, wherein:
  i) the active pharmaceutical ingredient and the glass-solution and/or eutectic-mixture forming additive(s) are dissolved in one or more solvents and rapidly mixed with an anti-solvent using an impinging jet mixer;
  ii) the slurry obtained in step i) is stirred for a period of time below ambient temperature to at least partially crystallize the active pharmaceutical ingredient;
  iii) the crystalline suspension obtained from step ii) is optionally warmed to re-dissolve a portion of the crystallized active pharmaceutical ingredient; and
  iv) the crystalline suspension from step ii) or iii) is spray dried under vacuum at or above ambient temperature to obtain a hybrid solid dispersion.

15. The composition of claim 1, wherein
  i) the active pharmaceutical ingredient and the glass-solution and/or eutectic-mixture forming additive(s) are dissolved in one or more solvents and rapidly mixed with an anti-solvent using an impinging jet mixer;
  ii) the slurry obtained in step i) is stirred below ambient temperature to at least partially crystallize the active pharmaceutical ingredient;
  iii) the crystalline suspension obtained from step ii) is optionally warmed to re-dissolve a portion of the crystallized active pharmaceutical ingredient; and
  iv) the crystalline suspension from step ii) or iii) is spray dried under vacuum at or above ambient temperature to obtain a hybrid solid dispersion.

16. A method for manufacturing a pharmaceutical composition having high drug loading, improved drug dissolution and stability, and reduced drug-drug or drug-excipient interaction comprising preparing a dosage form by filling the composition of claims 1 into a capsule or by compressing the composition of claim 1 into a tablet.

17. The composition according to claim 1, wherein the active pharmaceutical ingredient is present in an amount of from about 55% w/w to about 90% w/w with respect to the total amount of the active pharmaceutical ingredient and the pharmaceutically acceptable glass-solution forming and/or eutectic-mixture forming additives in the pharmaceutical composition.

18. The composition according to claim 1, wherein the active pharmaceutical ingredient is present in an amount of from about 60% w/w to about 90% w/w with respect to the total amount of the active pharmaceutical ingredient and the pharmaceutically acceptable glass-solution forming and/or eutectic-mixture forming additives in the pharmaceutical composition.

19. The composition according to claim 1, wherein the active pharmaceutical ingredient is present in an amount of from about 65% w/w to about 90% w/w with respect to the total amount of the active pharmaceutical ingredient and the pharmaceutically acceptable glass-solution forming and/or eutectic-mixture forming additives in the pharmaceutical composition.

* * * * *